US010750935B2

(12) United States Patent
Kawano

(10) Patent No.: US 10,750,935 B2
(45) Date of Patent: Aug. 25, 2020

(54) GUIDANCE DEVICE AND CAPSULE MEDICAL DEVICE GUIDANCE SYSTEM

(71) Applicant: OLYMPUS CORPORATION, Tokyo (JP)

(72) Inventor: Hironao Kawano, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 618 days.

(21) Appl. No.: 15/441,596

(22) Filed: Feb. 24, 2017

(65) Prior Publication Data

US 2017/0164816 A1 Jun. 15, 2017

Related U.S. Application Data

(63) Continuation of application No. PCT/JP2015/085769, filed on Dec. 22, 2015.

(30) Foreign Application Priority Data

Jan. 6, 2015 (JP) ................................ 2015-001180
Jan. 6, 2015 (JP) ................................ 2015-001181

(51) Int. Cl.
*A61B 1/00* (2006.01)
*G02B 23/24* (2006.01)
(Continued)

(52) U.S. Cl.
CPC ............ *A61B 1/00158* (2013.01); *A61B 1/00* (2013.01); *A61B 1/00016* (2013.01);
(Continued)

(58) Field of Classification Search
CPC ... A61B 1/00158; A61B 1/00; A61B 1/00016; A61B 1/00032; A61B 1/00045;
(Continued)

(56) References Cited

U.S. PATENT DOCUMENTS 8,740,774 B2 * 6/2014 Takizawa ........... A61B 1/00082
128/899
9,039,606 B2 * 5/2015 Uchiyama .......... A61B 1/00158
600/114
(Continued)

FOREIGN PATENT DOCUMENTS

CN 103222842 A 7/2013
CN 104203072 A 12/2014
(Continued)

OTHER PUBLICATIONS

International Search Report dated Mar. 29, 2016 issued in PCT/JP2015/085769.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A guidance device includes: a magnetic field generation unit configured to generate the magnetic field; a movement mechanism configured to move the magnetic field generation unit in a vertical direction; a rotation mechanism configured to rotate the magnetic field generation unit in a vertical plane including a magnetization direction of the magnetic field generation unit; an input unit configured to input first operation information for changing posture of a capsule medical device; and a control unit configured to: cause the rotation mechanism to rotate the magnetic field generation unit to change the posture of the capsule medical device based on the first operation information; and control the movement mechanism to change a distance between the magnetic field generation unit and the capsule medical device to correct a magnetic attracting force in a vertical direction of the capsule medical device.

8 Claims, 21 Drawing Sheets

(51) Int. Cl.
    *A61B 5/07*         (2006.01)
    *A61B 5/06*         (2006.01)
    *G06T 7/70*         (2017.01)
    *A61B 1/04*         (2006.01)
    *H04N 5/225*       (2006.01)
    *A61B 5/145*       (2006.01)
    *A61B 5/00*         (2006.01)

(52) U.S. Cl.
    CPC ...... *A61B 1/00032* (2013.01); *A61B 1/00045* (2013.01); *A61B 1/041* (2013.01); *A61B 5/062* (2013.01); *A61B 5/073* (2013.01); *G02B 23/24* (2013.01); *G02B 23/2476* (2013.01); *G06T 7/70* (2017.01); *H04N 5/2256* (2013.01); *A61B 5/14539* (2013.01); *A61B 5/4255* (2013.01); *A61B 5/6861* (2013.01); *H04N 2005/2255* (2013.01)

(58) Field of Classification Search
    CPC ......... A61B 1/041; A61B 5/062; A61B 5/073; A61B 5/14539; A61B 5/4255; A61B 5/6861; G02B 23/24; G02B 23/2476; G06T 7/70; H04N 5/2256; H04N 2005/2255
    See application file for complete search history.

(56) References Cited

U.S. PATENT DOCUMENTS

| | | | | |
|---|---|---|---|---|
| 9,155,450 | B2 | | 10/2015 | Kawano |
| 9,208,564 | B2 | * | 12/2015 | Degenhardt ....... A61B 1/00158 |
| 9,826,904 | B2 | * | 11/2017 | Valdastri ................. A61B 5/11 |
| 10,228,428 | B2 | * | 3/2019 | Gustafsson .......... G01R 33/072 |
| 2004/0204630 | A1 | * | 10/2004 | Gilad .................... A61B 1/041 600/160 |
| 2006/0152309 | A1 | * | 7/2006 | Mintchev .......... A61B 1/00158 335/58 |
| 2008/0300458 | A1 | | 12/2008 | Kim et al. |
| 2009/0012363 | A1 | * | 1/2009 | Liu ..................... A61B 1/00158 600/127 |
| 2010/0010304 | A1 | | 1/2010 | Kawano |
| 2010/0010306 | A1 | | 1/2010 | Kawano et al. |
| 2011/0184235 | A1 | * | 7/2011 | Schostek .......... A61B 1/00158 600/109 |
| 2011/0301497 | A1 | * | 12/2011 | Shachar ........... A61B 1/00158 600/567 |
| 2012/0095290 | A1 | | 4/2012 | Kawano |
| 2013/0304446 | A1 | * | 11/2013 | Rabinovitz ........ A61B 1/00158 703/11 |
| 2014/0148643 | A1 | | 5/2014 | Kawano |
| 2014/0288416 | A1 | | 9/2014 | Mahoney et al. |
| 2015/0018614 | A1 | | 1/2015 | Duan et al. |
| 2015/0018615 | A1 | | 1/2015 | Duan et al. |

FOREIGN PATENT DOCUMENTS

| | | |
|---|---|---|
| EP | 2 987 447 A1 | 2/2016 |
| EP | 2 995 240 A1 | 3/2016 |
| JP | 2008-503310 A | 2/2008 |
| JP | 2010-017554 A | 1/2010 |
| WO | WO 2011/118253 A1 | 9/2011 |
| WO | WO 2013/168681 A1 | 11/2013 |
| WO | 2014/169504 A1 | 10/2014 |

OTHER PUBLICATIONS

Extended Supplementary European Search Report dated Mar. 2, 2018 in European Patent Application No. 15 87 7033.9.

* cited by examiner

FIG.9
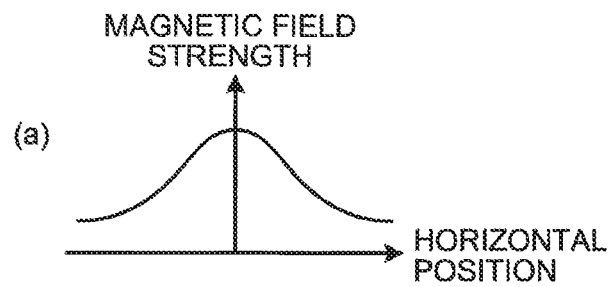
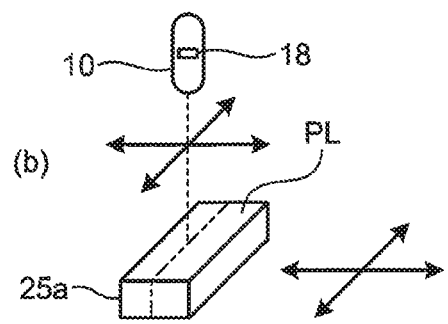
FIG.10
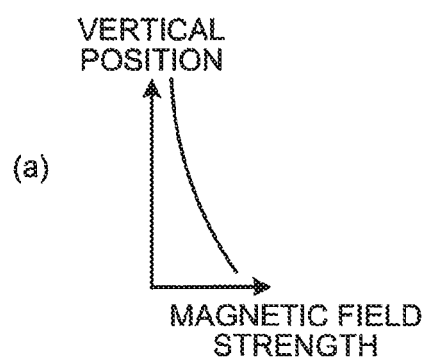
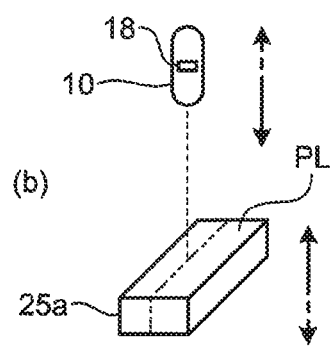

FIG.11
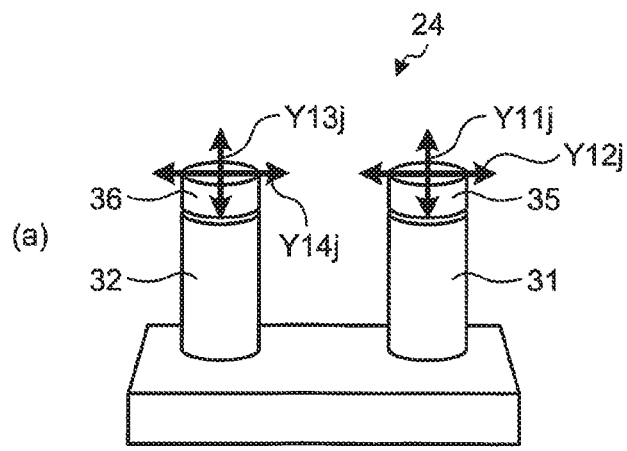
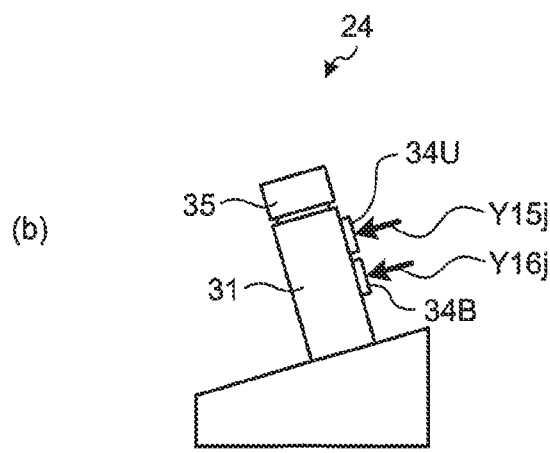
FIG.12
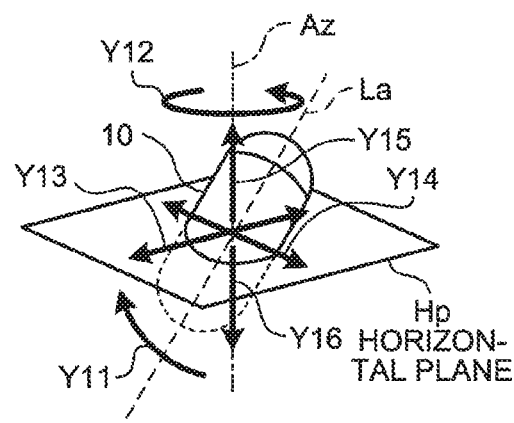

FIG.18
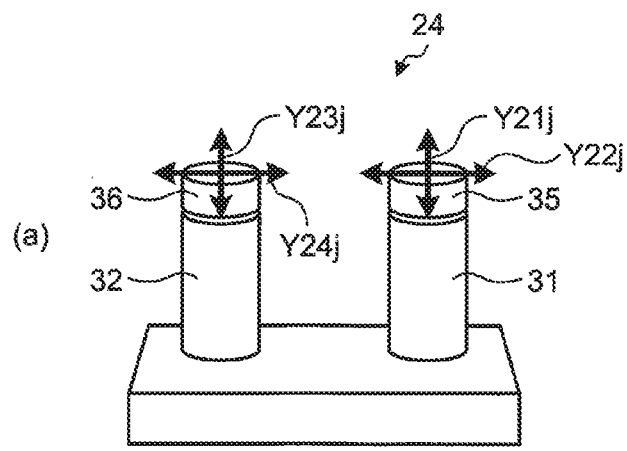
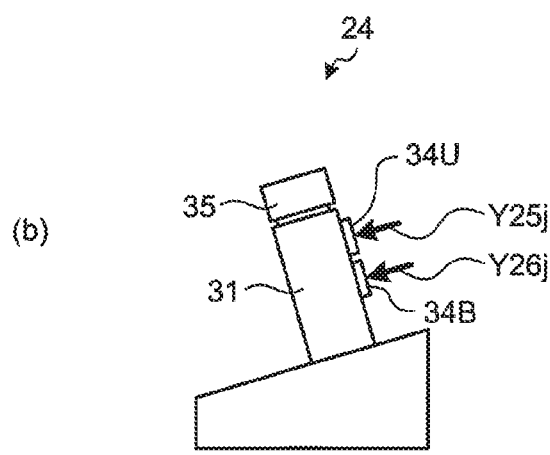
FIG.19
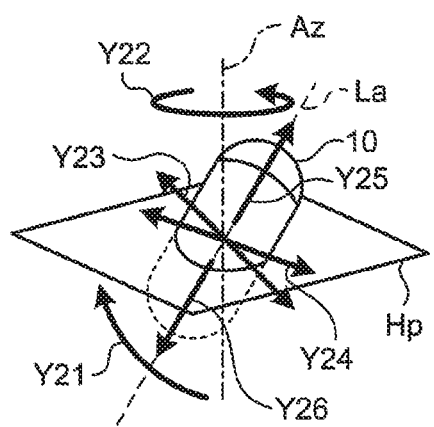

GUIDANCE DEVICE AND CAPSULE MEDICAL DEVICE GUIDANCE SYSTEM

CROSS-REFERENCE TO RELATED APPLICATIONS

This application is a continuation of PCT international application Ser. No. PCT/JP2015/085769 filed on Dec. 22, 2015 which designates the United States, incorporated herein by reference, and which claims the benefit of priority from Japanese Patent Application No. 2015-001180 filed on Jan. 6, 2015 and Japanese Patent Application No. 2015-001181 filed on Jan. 6, 2015, incorporated herein by reference.

BACKGROUND

1. Technical Field

The disclosure relates to a guidance device and a capsule medical device guidance system which guides a capsule medical device introduced into a subject.

2. Related Art

Capsule medical devices have been developed, each of which is introduced into a subject to obtain various kinds of information about the subject, or administer medication or the like to the subject. As an example, a capsule endoscope is known which is formed in a size small enough to be introduced into the subject's digestive tract.

The capsule endoscope includes an imaging function and wireless communication function in a capsule-shaped casing to perform imaging while moving in the digestive tract with peristaltic motion or the like, after being swallowed into the subject, and wirelessly transmit sequential image data of images of an organ inside the subject (hereinafter, also referred to as in-vivo image). The wirelessly transmitted image data is received by a receiving device provided outside the subject, and further captured into an image display device, such as a workstation, to be subjected to image processing. Thus, the in-vivo image of the subject can be displayed as a still image or a moving image.

In recent years, guidance systems have been proposed, each of which includes a guidance device for guiding a capsule endoscope introduced into a subject by a magnetic attracting force (hereinafter, referred to as magnetic guidance) (e.g., see JP 2008-503310 W and JP 2010-17554 A). Such a guidance system commonly has a configuration in which the capsule endoscope is internally provided with a permanent magnet, and the guidance device is provided with a magnetic field generation unit, such as an electromagnet or a permanent magnet, so that a magnetic attracting force of a magnetic field generated by the magnetic field generation unit magnetically guides the capsule endoscope in the subject. The guidance system is provided with a display unit for receiving image data obtained by the capsule endoscope and displaying an in-vivo image, and thus, a user can use an operation input unit provided in the guidance device to control magnetic guidance of the capsule endoscope, while referring to the in-vivo image displayed on the display unit.

SUMMARY

In some embodiments, a guidance device for guiding a capsule medical device having a magnet and introduced into a subject is provided. The guidance device includes: a magnetic field generation unit configured to generate the magnetic field for guiding the capsule medical device; a movement mechanism configured to move the magnetic field generation unit in a vertical direction; a rotation mechanism configured to rotate the magnetic field generation unit in a vertical plane including a magnetization direction of the magnetic field generation unit; an input unit configured to input first operation information for changing posture of the capsule medical device; and a control unit configured to: cause the rotation mechanism to rotate the magnetic field generation unit to change the posture of the capsule medical device based on the first operation information; and control the movement mechanism to change a distance between the magnetic field generation unit and the capsule medical device to correct a magnetic attracting force in a vertical direction of the capsule medical device, the magnetic attracting force being caused by the magnetic field generation unit rotated by the rotation mechanism.

In some embodiments, a capsule medical device guidance system includes: the capsule medical device in which the magnet is disposed; and the guidance device.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a schematic view illustrating a method of controlling a position of the capsule endoscope in a horizontal plane;

FIG. 10 is a schematic view illustrating a method of controlling a position of the capsule endoscope in a vertical direction;

FIG. 11 is a diagram illustrating an example of an operation input unit illustrated in FIG. 1;

FIG. 12 is a diagram for illustrating magnetic guidance of the capsule endoscope controlled by the operation input unit illustrated in FIG. 1;

FIG. 18 is a diagram illustrating an example of the operation input unit according to Modification 1-3 of the first embodiment;

FIG. 19 is a diagram for illustrating magnetic guidance of the capsule endoscope controlled by the operation input unit illustrated in FIG. 18;

DETAILED DESCRIPTION

Figure 1:
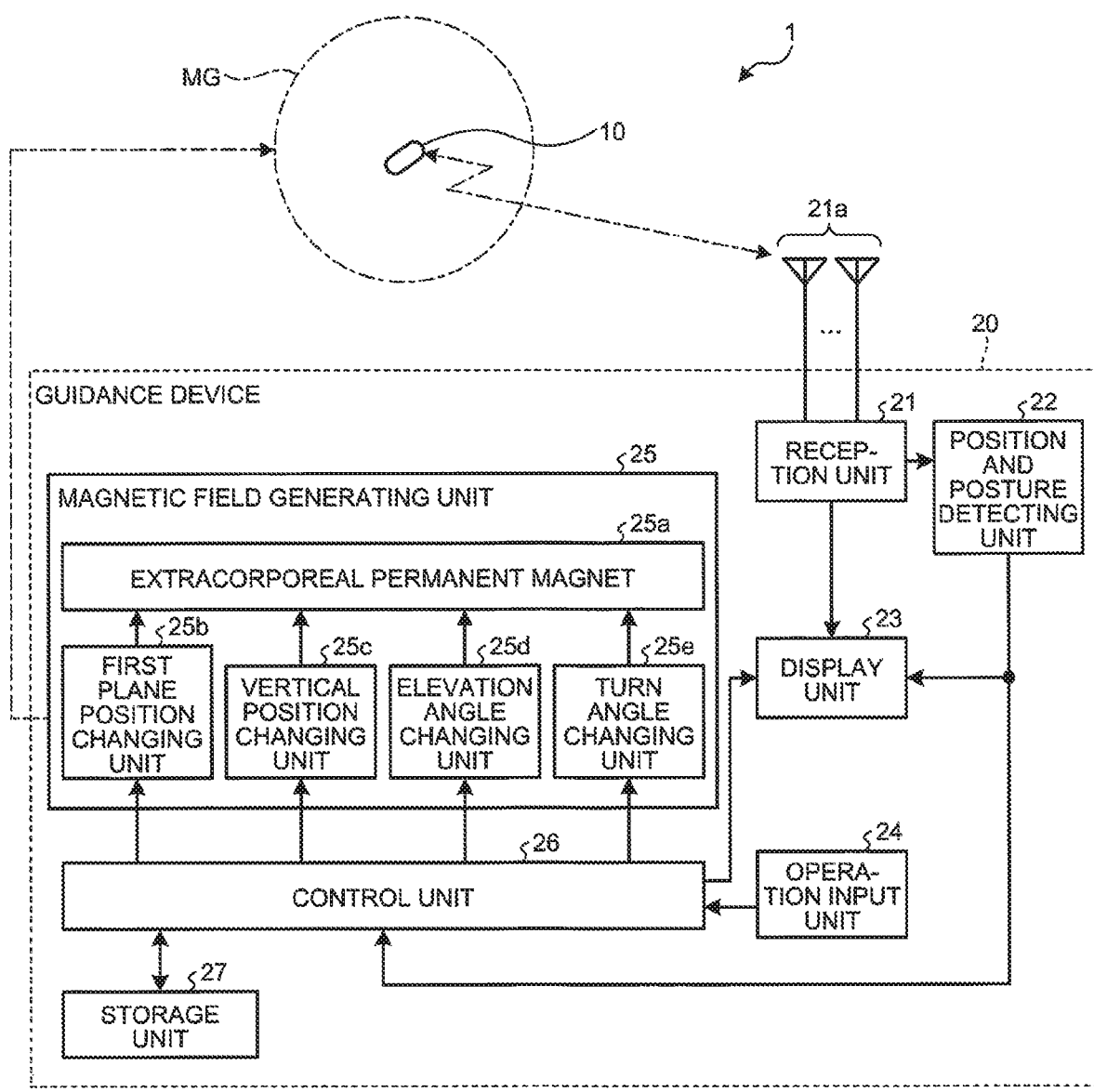
FIG. 1 is a diagram illustrating an exemplary configuration of a capsule medical device guidance system according to a first embodiment of the disclosure.

A capsule medical device guidance system according to an embodiment of the disclosure will be described below with reference to the drawings. It should be noted that, in the following description, as a form of a capsule medical device to be guided by a guidance device and a capsule medical device guidance system according to the present embodiment, a capsule endoscope orally introduced into a subject to capture inside the subject (in a lumen) is exemplified, but the present invention is not limited to this embodiment. That is, the present invention can be applied to magnetic guidance of various medical devices having a capsule shape, such as a capsule endoscope moving in a lumen of the subject, from esophagus to anus, a capsule medical device delivering medication or the like in the subject, or a capsule medical device including a PH sensor for measuring PH in the subject.

Furthermore, in the following description, the drawings merely schematically illustrate shapes, sizes, and positional relationships to the extent that the contents of the present invention can be understood. Accordingly, the present invention is not limited only to the shapes, sizes, and positional relationships exemplified in the drawings. Note that, in the drawings, the same portions are denoted by the same reference signs.

First Embodiment

Figure 2:
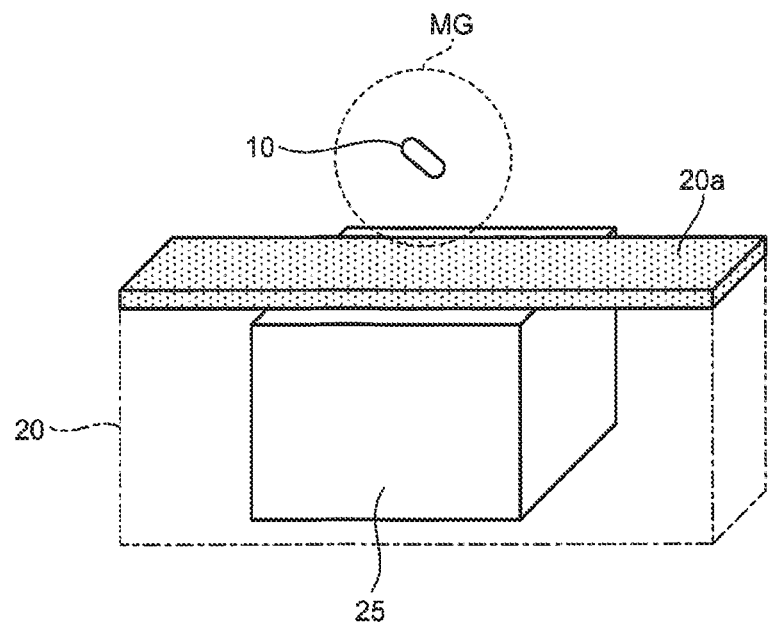
FIG. 2 is a schematic perspective view of an example of appearance of a guidance device illustrated in FIG. 1.

FIG. 1 is a schematic diagram illustrating an exemplary configuration of a capsule medical device guidance system according to a first embodiment of the disclosure. FIG. 2 is a schematic perspective view of an example of appearance of the guidance device illustrated in FIG. 1. As illustrated in FIG. 1, a capsule medical device guidance system 1 according to the present first embodiment includes a capsule endoscope 10 being a capsule medical device introduced into a body cavity of the subject and internally provided with a permanent magnet, and a guidance device 20 generating a magnetic field MG to magnetically guiding the capsule endoscope 10 introduced into the subject.

The capsule endoscope 10 is orally introduced into an organ of the subject with a predetermined fluid, and then moves in a digestive tract, and finally discharged outside the subject. During the movement, the capsule endoscope 10 floats in the fluid introduced into the organ of the subject (e.g., in stomach), sequentially captures in-vivo images while being magnetically guided by a magnetic field MG, and sequentially wirelessly transmits image information (image data) corresponding to the captured in-vivo images. Note that, a detailed configuration of the capsule endoscope 10 will be described below.

The guidance device 20 includes a reception unit 21, a position and posture detecting unit 22, a display unit 23, an operation input unit 24, a magnetic field generating unit 25, a control unit 26, and a storage unit 27. The reception unit 21 performs wireless communication with the capsule endoscope 10 to receive a wireless signal including the image information obtained by the capsule endoscope 10, the position and posture detecting unit 22 detects a position and a posture of the capsule endoscope 10 in the subject, on the basis of the wireless signal received from the capsule endoscope 10, the display unit 23 obtains the image information from the wireless signal received by the reception unit 21, performs predetermined signal processing on the image information to display an in-vivo image on a screen, and displays the position of the capsule endoscope 10 in the subject, on the screen, the operation input unit 24 receives, for example, input information for instruction of various operations in the capsule medical device guidance system 1, the magnetic field generating unit 25 generates a magnetic field for guiding the capsule endoscope 10, the control unit 26 controls these units, and the storage unit 27 stores the image information or the like captured by the capsule endoscope 10.

FIG. 2 is a schematic perspective view illustrating the appearance of the guidance device 20. As illustrated in FIG. 2, the guidance device 20 is provided with a bed 20a, as a mounting stage on which the subject is mounted. Under the bed 20a, at least the magnetic field generating unit 25 generating the magnetic field MG is disposed.

The reception unit 21 includes a plurality of antennas 21a, and sequentially receives the wireless signals from the capsule endoscope 10 through these antennas 21a. The reception unit 21 selects an antenna receiving the highest field strength from these antennas 21a, and performs demodulation or the like on the wireless signals received from the capsule endoscope 10 through the selected antenna. Therefore, the reception unit 21 extracts in-vivo image data of the subject from each of the wireless signals. The reception unit 21 outputs an image obtained from an image signal including the extracted in-vivo image data to the display unit 23.

The position and posture detecting unit 22 detects the position and the posture of the capsule endoscope 10 in the subject, on the basis of the strength of the wireless signal received by the reception unit 21, generates information about the position (hereinafter, referred to as positional information) and information about the posture (hereinafter, referred to as posture information) of the capsule endoscope 10, and outputs the information to the display unit 23 and the control unit 26. Note that, the posture of the capsule endoscope 10 is expressed by an inclination angle of a major axis of the capsule endoscope 10 relative to a vertical direction (gravity direction).

The position and the posture of the capsule endoscope 10 can be found by for example appropriately setting an initial value for each of the position and the posture, and repeatedly performing calculation of an estimate of each of the position and the posture by the Gauss-Newton method, until a displacement amount between a calculated estimate and the last estimate has a value not more than a predetermined value (e.g., see JP 2007-283001 A).

The display unit 23 includes various displays such as a liquid crystal display, and generates a screen including the in-vivo image based on the in-vivo image data input from the reception unit 21, or other various kinds of information, and displays the screen on the display. Specifically, the display unit 23 displays for example a group of in-vivo images of the subject captured by the capsule endoscope 10, the position information and the posture information of the capsule endoscope 10, or information about guidance operation of the capsule endoscope 10 by the user. The display unit 23 may display the position and the posture of the capsule endoscope 10 estimated based on a magnetic field generated by the guidance device 20, or a position in the subject, corresponding to an in-vivo image being displayed on the screen, on the basis of a result of detection of the position and the posture performed by the position and posture detecting unit 22. Furthermore, the display unit 23 may display for example, a reduced in-vivo image selected according to control of the control unit 26, or patient information and examination information of the subject.

The operation input unit 24 includes an input device such as a joystick, a console including various buttons and various switches, or a keyboard, and receives various input information such as guidance instruction information for magnetically guiding the capsule endoscope 10, or setting information for setting a predetermined mode to the guidance device 20. The guidance instruction information is information for controlling the position or the posture of the capsule endoscope 10 to be magnetically guided, and specifically includes information or the like about operation of translating the capsule endoscope 10 in a horizontal direction or a vertical direction (translation operation), operation of changing an inclination angle of the major axis of the capsule endoscope 10 relative to a vertical direction (inclination angle changing operation), or operation of changing an azimuth angle (angle about vertical axis) of a field of view (imaging units 11A and 11B described later) of the capsule endoscope 10 (azimuth angle changing operation). Note that, in the following, the azimuth angle of the field of view is merely referred to as an azimuth angle. The operation input unit 24 inputs the received input information to the control unit 26. Operation information changing the posture of the capsule endoscope 10 is referred to as first operation information, and operation information moving the capsule endoscope 10 in the vertical direction is referred to as second operation information.

The magnetic field generating unit 25 generates a magnetic field for changing the position, the inclination angle, and the azimuth angle of the capsule endoscope 10 introduced into the subject, relative to the subject. More specifically, the magnetic field generating unit 25 includes an extracorporeal permanent magnet 25a that is served as a magnetic field generation unit for generating a magnetic field and that is a second magnet including a magnetic material, a first plane position changing unit 25b changing a position and a posture of the extracorporeal permanent magnet 25a, a vertical position changing unit 25c, an elevation angle changing unit 25d, and a turn angle changing unit 25e.

Figure 3:
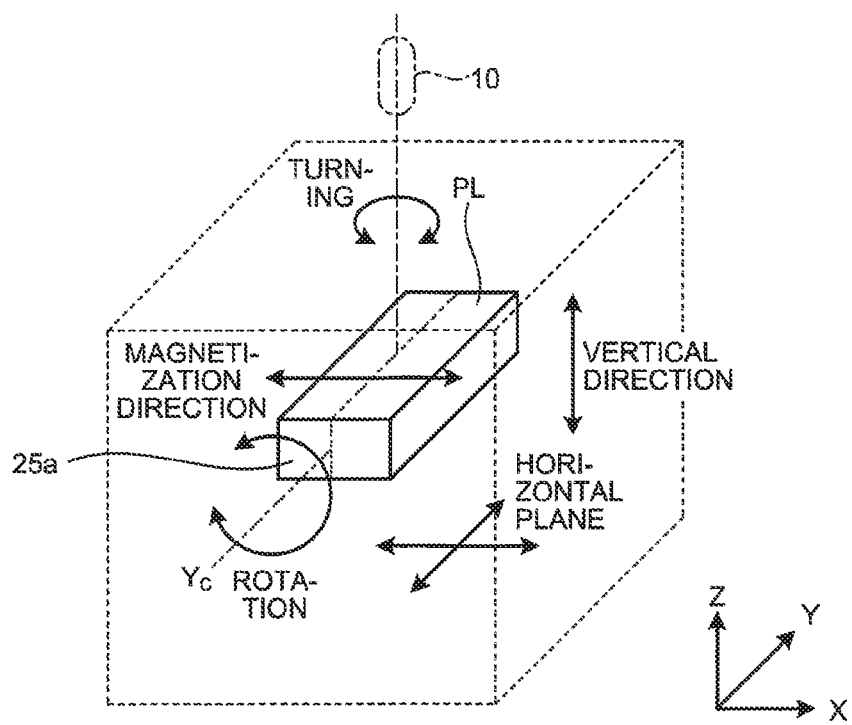
FIG. 3 is a schematic view illustrating an installation state of an extracorporeal permanent magnet illustrated in FIG. 1.

FIG. 3 is a schematic view illustrating an installation state of the extracorporeal permanent magnet 25a. As illustrated in FIG. 3, the extracorporeal permanent magnet 25a includes for example a bar magnet having a cuboid shape. In an initial state, the extracorporeal permanent magnet 25a is disposed so that one surface (hereinafter, also referred to as capsule facing surface PL) of four surfaces parallel with a magnetization direction of the extracorporeal permanent magnet 25a is parallel with a horizontal plane (plane orthogonal to gravity direction). Hereinafter, disposition of the extracorporeal permanent magnet 25a in the initial state is defined as a reference disposition, and in the reference disposition, the magnetization direction is defined as an X axis direction, a direction orthogonal to the magnetization direction in the horizontal plane is defined as a Y axis direction, and a vertical direction is defined as a Z axis direction.

The first plane position changing unit 25b translates the extracorporeal permanent magnet 25a in a horizontal plane (XY plane). That is, the extracorporeal permanent magnet 25a having two magnetized magnetic poles is moved in the horizontal plane while maintaining a relative position between the two magnetized magnetic poles.

The vertical position changing unit 25c is a translation mechanism translating the extracorporeal permanent magnet 25a in the vertical direction (Z direction) That is, the vertical position changing unit 25c moves the extracorporeal permanent magnet 25a in the vertical direction, while maintaining the two magnetized magnetic poles.

The elevation angle changing unit 25d is a rotation mechanism rotating the extracorporeal permanent magnet 25a in a vertical plane including the magnetization direction of the extracorporeal permanent magnet 25a to change an angle of the magnetization direction relative to the horizontal plane. In other words, the elevation angle changing unit 25d rotates the extracorporeal permanent magnet 25a about an axis (hereinafter, referred to as rotation axis $Y_C$) parallel with the capsule facing surface PL and orthogonal to the magnetization direction, and passing through the center of the extracorporeal permanent magnet 25a. Hereinafter, an angle between the magnetization direction of the extracorporeal permanent magnet 25a and the horizontal plane is defined as an elevation angle.

The turn angle changing unit 25e rotates the extracorporeal permanent magnet 25a about a vertical axis passing through the center of the extracorporeal permanent magnet 25a. Hereinafter, rotation movement of the extracorporeal permanent magnet 25a about the vertical axis is referred to as turning movement. Furthermore, an angle through which the extracorporeal permanent magnet 25a turns relative to the reference disposition is defined as a turn angle.

When the extracorporeal permanent magnet 25a is rotated about the rotation axis $Y_C$, by the elevation angle changing unit 25d, while the extracorporeal permanent magnet 25a is turned by the turn angle changing unit 25e by the turn angle to change an angle of the rotation axis $Y_C$ relative to the reference disposition, the inclination angle and the azimuth angle of the capsule endoscope 10 restrained in the magnetic field generated by the extracorporeal permanent magnet 25a can be changed.

The control unit 26 controls operation of each unit of the magnetic field generating unit 25, on the basis of a detection result from the position and posture detecting unit 22, and guidance instruction information received by the operation input unit 24, to change a relative position between the extracorporeal permanent magnet 25a and the subject, a distance between the extracorporeal permanent magnet 25a and the capsule endoscope 10, or rotation angles (elevation angle and turn angle) of the extracorporeal permanent magnet 25a relative to the reference disposition, and guides the capsule endoscope 10 to a user's desired position and posture. At that time, the control unit 26 calculates a correction amount of the distance between the capsule endoscope 10 and the extracorporeal permanent magnet 25a to prevent generation of change in position of the capsule endoscope 10 caused by rotation of the extracorporeal permanent magnet 25a (change in elevation angle), which is not intended by the user, and uses the correction amount to control each unit of the magnetic field generating unit 25.

The storage unit 27 includes a storage medium rewritably storing information, such as flash memory or a hard disk. The storage unit 27 stores information such as various programs or various parameters for controlling each unit of the guidance device 20 by the control unit 26, in addition to image data of the group of in-vivo images of the subject captured by the capsule endoscope 10.

Figure 4:
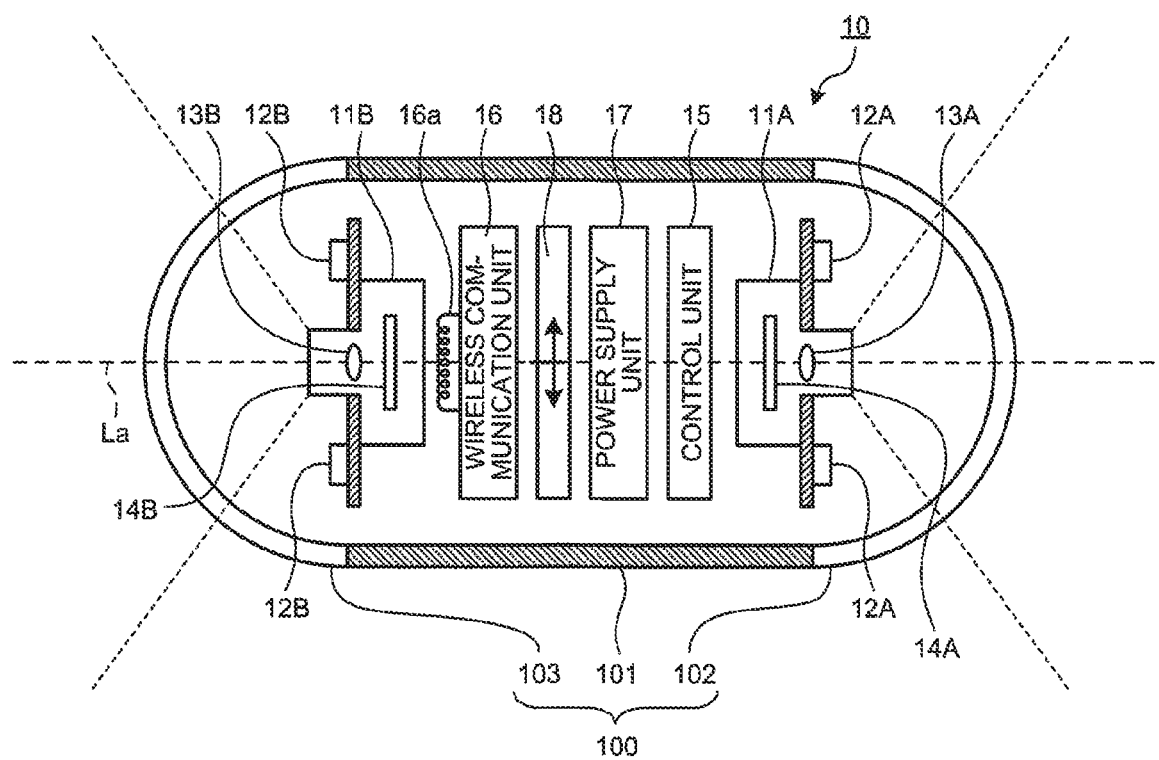
FIG. 4 is a schematic view illustrating an example of an inner structure of a capsule endoscope illustrated in FIG. 1.

Next, a detailed configuration of the capsule endoscope 10 will be described. FIG. 4 is a schematic view illustrating an example of an inner structure of the capsule endoscope 10. As illustrated in FIG. 4, the capsule endoscope 10 includes a capsule-shaped casing 100 being an outer cover formed in a sufficient size to be introduced into the organ of the subject, and the imaging units 11A and 11B capturing images of the object in different imaging directions. Furthermore, the capsule endoscope 10 includes a control unit 15 processing signals input from the imaging units 11A and 11B, and controlling each component unit of the capsule endoscope 10, a wireless communication unit 16 wirelessly transmitting the signals processed by the control unit 15, outside the capsule endoscope 10, and a power supply unit 17 supplying power to each component unit of the capsule endoscope 10. Furthermore, the capsule endoscope 10 includes a permanent magnet 18 being a first magnet allowing magnetic guidance by the guidance device 20.

The capsule-shaped casing 100 is an outer casing formed in a sufficient size to be introduced into the organ of the subject, includes a cylindrical casing 101 and domed casings 102 and 103, and is configured to close both side opening ends of the cylindrical casing 101 with the domed casings 102 and 103. The cylindrical casing 101 is a colored casing substantially opaque to visible light. Furthermore, the domed casings 102 and 103 are dome shaped optical members transparent to light of a predetermined wavelength band, such as visible light. As illustrated in FIG. 4, such a capsule-shaped casing 100 liquid-tightly encapsulates the imaging units 11A and 11B, the control unit 15, the wireless communication unit 16, the power supply unit 17, and the permanent magnet 18.

The imaging unit 11A has an illumination unit 12A such as LED, an optical system 13A such as a condenser lens, and an imaging element 14A such as a CMOS image sensor or a CCD. The illumination unit 12A emits illumination light such as white light to a field of view of the imaging element 14A, and illuminates the subject in the field of view, through the domed casing 102. The optical system 13A focuses reflected light from the field of view, on an imaging surface of the imaging element 14A, and forms an object image in the field of view, on the imaging surface of the imaging element 14A. The imaging element 14A receives the reflected light from the field of view, through the imaging surface, performs photoelectric conversion on the received optical signal, and captures the object image in the field of view, that is, an in-vivo image of the subject.

Similarly to the imaging unit 11A, the imaging unit 11B has an illumination unit 12B such as an LED, an optical system 13B such as a condenser lens, and an imaging element 14B such as a CMOS image sensor or a CCD, and images the subject in the field of view through the domed casing 103.

As illustrated in FIG. 4, when the capsule endoscope 10 is a capsule medical device having two lenses capturing forward and rearward portions in a direction of the major axis La, the imaging units 11A and 11B are disposed to have optical axes each substantially parallel with or coinciding with a major axis La being a longitudinal axis of the capsule-shaped casing 100, and to have fields of view directed in opposite directions. That is, the imaging units 11A and 11B are mounted so that the imaging surfaces of the imaging elements 14A and 14B are orthogonal to the major axis La.

The control unit 15 controls the operations of the imaging units 11A and 11B and the wireless communication unit 16, and controls input and output of the signals between these units. Specifically, the control unit 15 causes the imaging element 14A to capture the image of the object in the field of view illuminated by the illumination unit 12A, and causes the imaging element 14B to capture the image of the object in the field of view illuminated by the illumination unit 12B. Then, the control unit 15 obtains the in-vivo image data from the imaging elements 14A and 14B, performs predetermined signal processing on the in-vivo image data whenever obtaining the in-vivo image data, and generates the image signals including the in-vivo image data. Furthermore, the control unit 15 sequentially wirelessly transmits the image signals including the in-vivo image data in time-series, to the wireless communication unit 16.

The wireless communication unit 16 includes an antenna 16a for transmitting the wireless signal. The wireless communication unit 16 obtains the image signals of the in-vivo images of the subject captured by the imaging units 11A and 11B from the control unit 15, and performs modulation or the like on the image signals to generate the wireless signals. Then, the wireless signals are transmitted through the antenna 16a.

The power supply unit 17 is a power storage unit such as a button battery or a capacitor, and has a switch portion such as a magnetic switch or an optical switch. When the power supply unit 17 is configured to have the magnetic switch, power is turned on and off by a magnetic field applied from outside, and when the power is turned on, the power of the power storage unit is appropriately supplied to component units (the imaging units 11A and 11B, the control unit 15, and the wireless communication unit 16) of the capsule endoscope 10. Furthermore, the power supply unit 17 being turned off stops power supply to the component units of the capsule endoscope 10.

The permanent magnet 18 is used to allow magnetic guidance of the capsule endoscope 10 by the magnetic field MG generated by the magnetic field generating unit 25, and is fixedly disposed in the capsule-shaped casing 100 so that a magnetization direction is inclined relative to the major axis La. Note that, in FIG. 4, the magnetization direction of the permanent magnet 18 is indicated by an arrow. In the present first embodiment, the permanent magnet 18 is disposed so that the magnetization direction is orthogonal to the major axis La. The permanent magnet 18 operates following the magnetic field applied from outside and thus the magnetic guidance of the capsule endoscope 10 by the magnetic field generating unit 25 is achieved.

Figure 5:
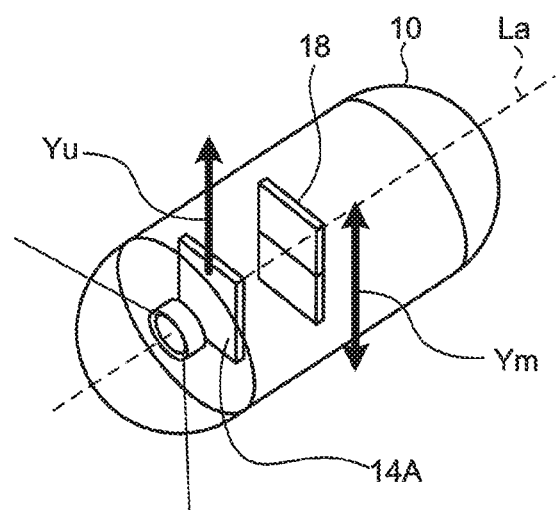
FIG. 5 is a schematic view illustrating a relative positional relationship between an imaging element and a permanent magnet in the capsule endoscope.

Here, a relative positional relationship between the imaging element 14A and the permanent magnet 18 will be described with reference to FIG. 5. The permanent magnet 18 fixed relative to the imaging unit 11A is fixedly disposed in the capsule-shaped casing 100. More specifically, the permanent magnet 18 is disposed so that the magnetization direction of the permanent magnet 18 is fixed relative to an up and down direction of the imaging surface of the imaging element 14A. Specifically, as illustrated in FIG. 5, the permanent magnet 18 is disposed so that the magnetization direction Ym of the permanent magnet 18 is parallel with the up and down direction Yu of the imaging surface of the imaging element 14A. A relative positional relationship between the imaging element 14B and the permanent magnet 18 is the same as the relative positional relationship between the imaging element 14A and the permanent magnet 18.

Figure 6:
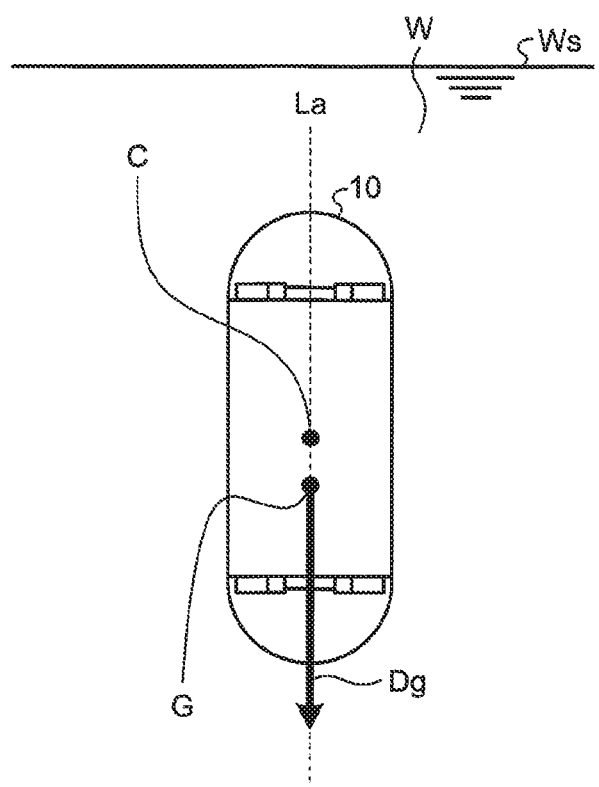
FIG. 6 is a conceptual diagram illustrating a state of the capsule endoscope while fluid is introduced into a subject (without application of a magnetic field)

FIG. 6 is a conceptual diagram illustrating a state of the capsule endoscope 10 while the fluid W is introduced into the subject. Note that, FIG. 6 illustrates a state in which the magnetic field from the magnetic field generating unit 25 for controlling the position and the posture of the capsule endoscope 10 is not applied to the permanent magnet 18 in the capsule-shaped casing.

The capsule endoscope 10 exemplified in the present first embodiment has a specific weight smaller than the specific weight of the fluid W, and is designed to float in the fluid W while the magnetic field from the magnetic field generating unit 25 is not applied. Furthermore, the capsule endoscope 10 has a center of gravity G which is set to be located at a position on the major axis La of the capsule endoscope 10 (longitudinal axis of the capsule endoscope 10: see FIG. 4), displaced from a geometric center C of the capsule endoscope 10. In the present first embodiment, the center of gravity G of the capsule endoscope 10 is set to a position on the major axis La, displaced from the geometric center C of the capsule-shaped casing 100 toward the imaging unit 11B, by adjusting the disposition of the component units, such as the power supply unit 17 and the permanent magnet 18. Therefore, the capsule endoscope 10 floats in the fluid W while maintaining the major axis La of the capsule endoscope 10 substantially parallel with a vertical direction. In other words, the capsule endoscope 10 floats in the fluid W while maintaining a straight line connecting the geometric center C and the center of gravity G in an upright position. In the capsule endoscope 10 having such an upright posture, the field of view of the imaging unit 11A is directed vertically upward, and the field of view of the imaging unit 11B is directed vertically downward. Note that, the fluid W is a fluid harmless to human, such as water or saline.

Furthermore, as described above, the permanent magnet 18 is disposed so that the magnetization direction Ym (see FIG. 5) is orthogonal to the major axis La. That is, the magnetization direction Ym of the permanent magnet 18 coincides with a radial direction of the capsule endoscope 10. Accordingly, the magnetic field for controlling the position and the posture of the capsule endoscope 10 is not applied to the permanent magnet 18, the capsule endoscope 10 floats in the fluid W, while the magnetization direction Ym coincides with the horizontal direction. Furthermore, at this time, a plane passing the magnetization direction Ym and the line connecting the geometric center C of the capsule-shaped casing 100 and the center of gravity G is defined as a vertical plane.

Figure 7:
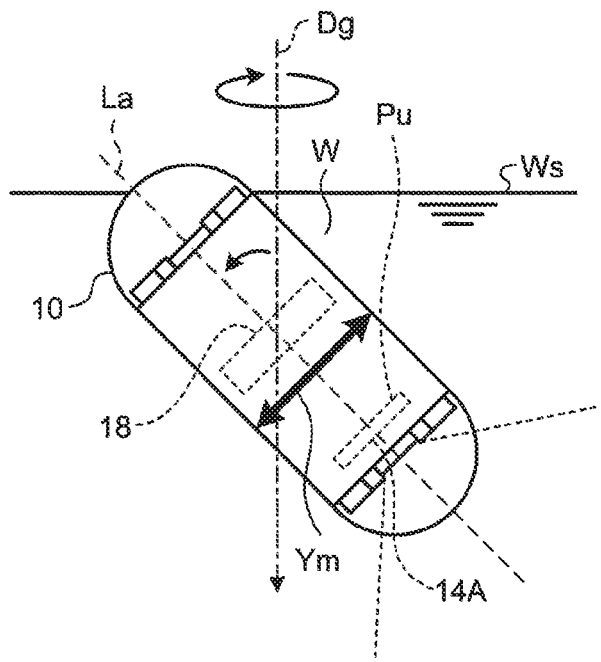
FIG. 7 is a conceptual diagram illustrating a state of the capsule endoscope while fluid is introduced into the subject (with application of the magnetic field)

FIG. 7 is a conceptual diagram illustrating a state of the capsule endoscope 10 while the fluid W is introduced into the subject, in which a magnetic field for controlling the inclination angle of the capsule endoscope 10 is applied to the permanent magnet 18.

As illustrated in FIG. 7, inclination of the major axis La of the capsule endoscope 10 relative to the gravity direction Dg can be controlled by applying a magnetic field from outside the permanent magnet 18 of the capsule endoscope 10. For example, application of a magnetic field in which a direction of a magnetic line of force has an angle relative to the horizontal plane, to the permanent magnet 18 can incline the capsule endoscope 10 relative to the gravity direction Dg so that the magnetization direction Ym of the permanent magnet 18 is substantially parallel with the magnetic line of force. In this state, the posture of the capsule endoscope 10 is changed while the magnetization direction Ym is included in the vertical plane. The magnetic field performing such control is achieved by rotating the extracorporeal permanent magnet 25a by the elevation angle changing unit 25d of the guidance device 20 (see FIGS. 1 and 3).

Accordingly, when the capsule endoscope 10 being inclined is turned about the gravity direction Dg as indicated by an arrow, by application of a magnetic field turning about the gravity direction Dg, the in-vivo images around the capsule endoscope 10 can be readily obtained. The magnetic field performing such control is achieved by turning the extracorporeal permanent magnet 25a by the turn angle changing unit 25e of the guidance device 20 (see FIGS. 1 and 3).

Figure 8:
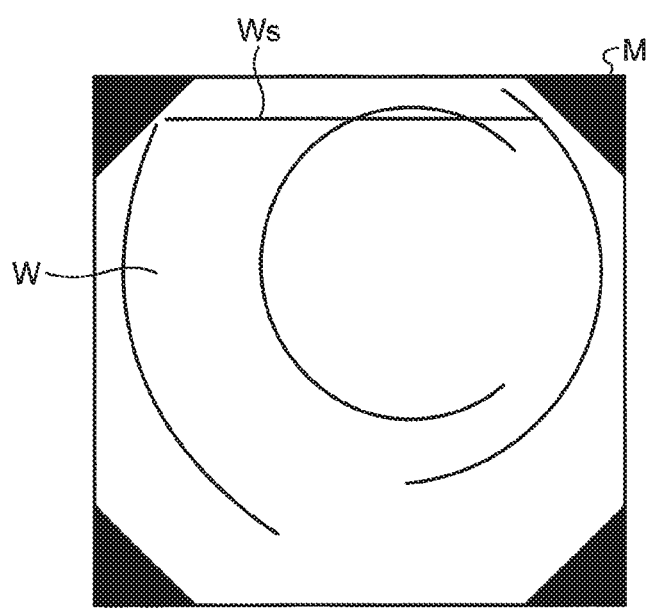
FIG. 8 is a diagram illustrating an example of an image displayed on a display screen of a display unit illustrated in FIG. 1.

At this time, the display unit 23 of the guidance device 20 displays the in-vivo images of the subject from the capsule endoscope 10 in a display mode in which an up and down direction of the object in the in-vivo image during the magnetic guidance of the capsule endoscope 10 coincide with an up and down direction of a display screen. As a result, as illustrated in FIG. 8, the display screen M of the display unit 23 displays a fluid surface Ws imaged by elements in an upper area Pu of the imaging element 14A of the capsule endoscope 10 so that the fluid surface Ws is positioned at an upper portion of an image corresponding to the imaging unit 11A. Since the magnetization direction Ym of the permanent magnet 18 is parallel with the up and down direction Yu of each of the imaging surfaces of the imaging elements 14A and 14B, a direction parallel with the magnetization direction Ym of the permanent magnet 18 coincides with the up and down direction of the display screen M of the display unit 23.

As illustrated in FIG. 9, translation movement of the capsule endoscope 10 in the horizontal plane can be controlled by applying a magnetic field having a peak field strength in the capsule facing surface PL (see (a) of FIG. 9) to the permanent magnet 18 of the capsule endoscope 10, and attracting the permanent magnet 18 to a position of the peak magnetic field to restrain the capsule endoscope 10 (see (b) of FIG. 9). Specifically, such a magnetic field is achieved by moving the extracorporeal permanent magnet 25a in the horizontal plane by the first plane position changing unit 25b of the guidance device 20.

As illustrated in FIG. 10, the translation movement of the capsule endoscope 10 in the vertical direction can be controlled by applying a magnetic field, in which a magnetic field gradient distribution changes according to a distance in a direction orthogonal to the capsule facing surface PL, to the permanent magnet 18 of the capsule endoscope 10. Specifically, such a magnetic field is achieved by moving the extracorporeal permanent magnet 25a in the vertical direction by the vertical position changing unit 25c of the guidance device 20.

For example, as illustrated in (a) of FIG. 10, when the capsule facing surface PL is positioned horizontally, a magnetic field having a magnetic gradient decreasing with increasing vertical position is applied to the permanent magnet 18. At this time, as illustrated in (b) of FIG. 10, when the extracorporeal permanent magnet 25a is moved upward (see solid arrow) to relatively reduce the vertical position of the permanent magnet 18, a magnetic attracting force generated in the permanent magnet 18 is increased, and the capsule endoscope 10 is urged downward (same as above). In contrast, when the extracorporeal permanent magnet 25a is moved downward (see dotted arrow) to relatively increase the vertical position of the permanent magnet 18, a magnetic attracting force generated in the permanent magnet 18 decreases, and the capsule endoscope 10 is urged upward (same as above). Note that, the position of the capsule endoscope 10 in the vertical direction is stopped and maintained substantially at a position having well-balanced flotation of the capsule endoscope 10 relative to the fluid W, gravity on the capsule endoscope 10, and magnetic attracting force generated by the extracorporeal permanent magnet 25a.

Next, a specific configuration and operation of the operation input unit 24 illustrated in FIG. 1 will be described. A front view of the operation input unit 24 is illustrated in (a) of FIG. 11, and a right side view of the operation input unit 24 is illustrated in (b) of FIG. 11. FIG. 12 is a diagram illustrating movements of the capsule endoscope 10 which is designated by operation of component portions of the operation input unit 24.

As illustrated in (a) of FIG. 11, the operation input unit 24 includes two joysticks 31 and 32 for three-dimensionally controlling magnetic guidance of the capsule endoscope 10 through the magnetic field generating unit 25. The joysticks 31 and 32 can be operated to be tilted in up and down directions and right and left directions.

As illustrated in (b) of FIG. 11, the joystick 31 has a back surface provided with an up button 34U and a down button 34B. The up button 34U is pressed to input guidance instruction information for instruction of upward guidance of the capsule endoscope 10 to the control unit 26, and the down button 34B is pressed to input guidance instruction information for instruction of downward guidance of the capsule endoscope 10 to the control unit 26. The joystick 31 has an upper portion provided with a capture button 35. The capture button 35 is pressed to capture an in-vivo image displayed on the display unit 23. Furthermore, the joystick 32 has an upper portion provided with an approach button 36. The approach button 36 is pressed to input, to the control unit 26, guidance instruction information guiding the capsule endoscope 10 so that the imaging unit 11A side of the capsule endoscope 10 approaches an object to be imaged by the imaging unit 11A.

As illustrated in (a) of FIG. 11, up-and-down tilting directions of the joystick 31 indicated by an arrow Y11j corresponds to a tilting guidance direction in which a distal end of the capsule endoscope 10 swings to pass through a vertical axis Az, as indicated by an arrow Y11 of FIG. 12. When guidance instruction information corresponding to tilting operation of the joystick 31 indicated by the arrow Y11j is input from the operation input unit 24 to the control unit 26, the control unit 26 calculates a guidance direction of the distal end of the capsule endoscope 10 on an absolute coordinate system, corresponding to the tilting direction of the joystick 31, and calculates a guidance amount corresponding to the tilting operation of the joystick 31, on the basis of the guidance instruction information. Then, the magnetic field generating unit 25 controls the elevation angle changing unit 25d to change the elevation angle of the extracorporeal permanent magnet 25a, for example, in the calculated guidance direction, according to the calculated guidance amount.

As illustrated in (a) of FIG. 11, right-and-left tilting directions of the joystick 31 indicated by an arrow Y12j corresponds to a rotation guidance direction in which the capsule endoscope 10 rotates about the axis Az, as indicated by an arrow Y12 of FIG. 12. When guidance instruction information corresponding to tilting operation of the joystick 31 indicated by the arrow Y12j is input from the operation input unit 24 to the control unit 26, the control unit 26 calculates a guidance direction of the distal end of the capsule endoscope 10 on the absolute coordinate system, corresponding to the tilting direction of the joystick 31, and calculates a guidance amount corresponding to the tilting operation of the joystick 31, on the basis of the guidance instruction information, and controls the turn angle changing unit 25e to turn the extracorporeal permanent magnet 25a, for example, in the calculated guidance direction, according to the calculated guidance amount.

As illustrated in (a) of FIG. 11, up-and-down tilting directions of the joystick 32 indicated by an arrow Y13j correspond to horizontal backward guidance directions or horizontal forward guidance directions in which the capsule endoscope 10 moves in a direction of the major axis La projected on the horizontal plane Hp, as indicated by an arrow Y13 of FIG. 12. When guidance instruction information corresponding to tilting operation of the joystick 32 indicated by the arrow Y13j is input from the operation input unit 24 to the control unit 26, the control unit 26 calculates a guidance direction and a guidance amount of the distal end of the capsule endoscope 10 on the absolute coordinate system, corresponding to the tilting direction of the joystick 32, on the basis of the guidance instruction information, and controls the first plane position changing unit 25b to translate the extracorporeal permanent magnet 25a, according to the calculated guidance direction and guidance amount.

As illustrated in (a) of FIG. 11, right-and-left tilting directions of the joystick 32 indicated by an arrow Y14j correspond to a horizontal right guidance direction or a horizontal left guidance direction in which the capsule endoscope 10 moves orthogonally to a direction of the major axis La projected on the horizontal plane Hp, as indicated by an arrow Y14 of FIG. 12. When guidance instruction information corresponding to tilting operation of the joystick 32 indicated by the arrow Y14j is input from the operation input unit 24 to the control unit 26, the control unit 26 calculates a guidance direction and a guidance amount of the distal end of the capsule endoscope 10 on the absolute coordinate system, corresponding to the tilting direction of the joystick 32, on the basis of the guidance instruction information, and controls the first plane position changing unit 25b to translate the extracorporeal permanent magnet 25a, according to the calculated guidance direction and guidance amount.

Furthermore, the back surface of the joystick 31 is provided with the up button 34U and the down button 34B. As indicated by an arrow Y15j in (b) of FIG. 11, pressing the up button 34U designates up operation for upward movement along the axis Az illustrated in FIG. 12, as indicated by an arrow Y15. Furthermore, as indicated by an arrow Y16j in (b) of FIG. 11, when the down button 34B is pressed, downward operation is designated for downward movement along the axis Az illustrated in FIG. 12, as indicated by an arrow Y16.

When guidance instruction information corresponding to pressing operation of the up button 34U or the down button 34B indicated by the arrow Y15j or Y16j is input from the operation input unit 24 to the control unit 26, the control unit 26 calculates a guidance direction and a guidance amount of the distal end of the capsule endoscope 10 on the absolute coordinate system, corresponding to pressing of any of the buttons on the basis of the guidance instruction information, and controls the vertical position changing unit 25c to translate the extracorporeal permanent magnet 25a in the vertical direction, according to the calculated guidance direction and guidance amount. For example, when the up button 34U is pressed, the vertical position changing unit 25c translates the extracorporeal permanent magnet 25a downward along the axis Az (in a direction separated from the capsule endoscope 10). Thus, the capsule endoscope 10 is raised as indicated by the arrow Y15. In contrast, when the down button 34B is pressed, the vertical position changing unit 25c translates the extracorporeal permanent magnet 25a upward along the axis Az (in a direction approaching the capsule endoscope 10). Thus, the capsule endoscope 10 is lowered as indicated by the arrow Y16. Note that, the operation input unit 24 may further have an input device including various operation buttons, a keyboard, or the like, in addition to the joysticks 31 and 32.

Figure 13:
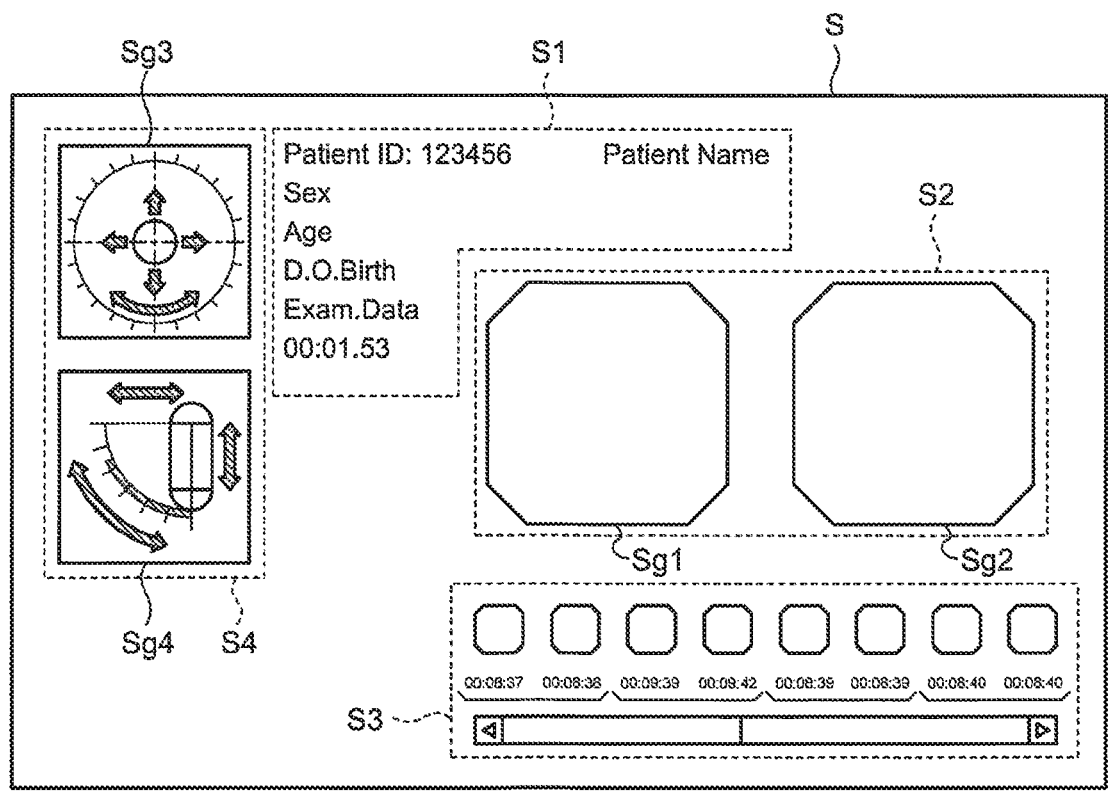
FIG. 13 is a diagram illustrating an example of a menu screen displayed on the display unit.

FIG. 13 is a schematic diagram illustrating an example of displaying a menu screen S displayed on the display unit 23. The menu screen S has an upper left area S1, in which subject information such as patient name, patient ID, date of birth, sex, age, and the like of the subject are displayed. Furthermore, in a center area S2, a biological image Sg1 captured by the imaging unit 11A is displayed on the left side, and a biological image Sg2 captured by the imaging unit 11B is displayed on the right side. In an area S3 below the area S2, images captured by pressing operation of the capture button 35 are displayed in a reduced size, together with capture time. In a left area S4, as a posture indicator of the capsule endoscope 10, a posture indicator Sg3 in a vertical plane and a posture indicator Sg4 in a horizontal plane are displayed.

The posture of the capsule endoscope 10 displayed in the posture indicators Sg3 and Sg4 represents a posture corresponding to the guidance instruction information from the operation input unit 24. In the present first embodiment, since the input amount from the operation input unit 24 is reflected on a force guiding the capsule endoscope 10, the displayed posture of the capsule endoscope 10 can be considered to be substantially the same as actual posture of the capsule endoscope 10, and aid for operator's guidance instruction is improved. Note that, in the posture indicators Sg3 and Sg4, a direction in which the capsule endoscope 10 can be guided is represented by an arrow, and when operation in any of the guidance directions is input, display color of an arrow corresponding to the input direction is changed to aid operator's operation.

Figure 14:
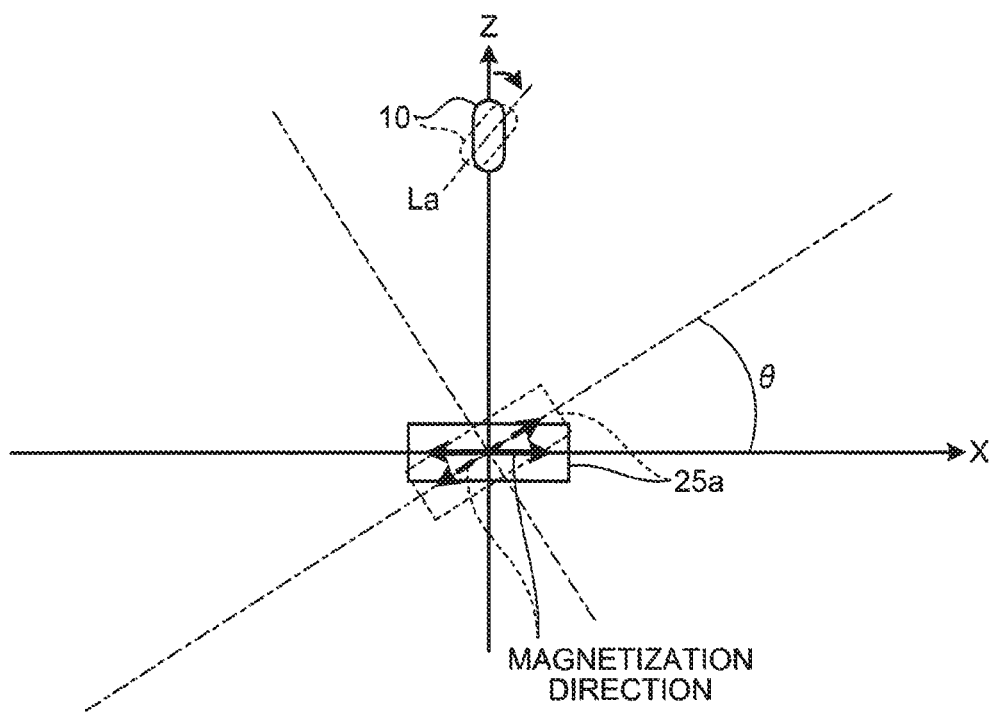
FIG. 14 is a conceptual diagram illustrating a principle of correction of a vertical magnetic attracting force generated in the capsule endoscope.

Next, operation of the control unit 26 to change the posture of the capsule endoscope 10 will be described in detail. Generally, given the same distance from the a permanent magnet, a strength of a magnetic field generated by the permanent magnet (i.e., magnetic attracting force generated in another magnetic material toward the permanent magnet) is maximum on an axis passing through the permanent magnet and parallel with a magnetization direction, and is minimum on an axis passing through the permanent magnet and orthogonal to the magnetization direction. For example, as illustrated in FIG. 14, when the extracorporeal permanent magnet 25a is disposed so that the magnetization direction is positioned along the X axis, the magnetic attracting force generated in the capsule endoscope 10 (the permanent magnet 18 built therein, to be exact) toward the extracorporeal permanent magnet 25a is maximum on the X axis, and minimum on the Z axis, wherein the magnetic attracting force is generated by the magnetic field generated by the extracorporeal permanent magnet 25a. The magnetic attracting force generated in the capsule endoscope 10 toward the extracorporeal permanent magnet 25a, which is generated by the magnetic field generated by the extracorporeal permanent magnet 25a is distributed to gradually increase from a position having a minimum strength to a position having a maximum strength.

Accordingly, when the capsule endoscope 10 floating in the fluid in an organ such as stomach is restrained vertically upward from the extracorporeal permanent magnet 25a disposed as described above, it can be said that the capsule endoscope 10 is restrained at a position having a minimum magnetic attracting force of the extracorporeal permanent magnet 25a.

Here, there is a problem that when the extracorporeal permanent magnet 25a is rotated to change the posture of the capsule endoscope 10, the restrained position of the capsule endoscope 10 is displaced from a user's intended position due to change of the magnetic field caused by the rotation.

Figure 15:
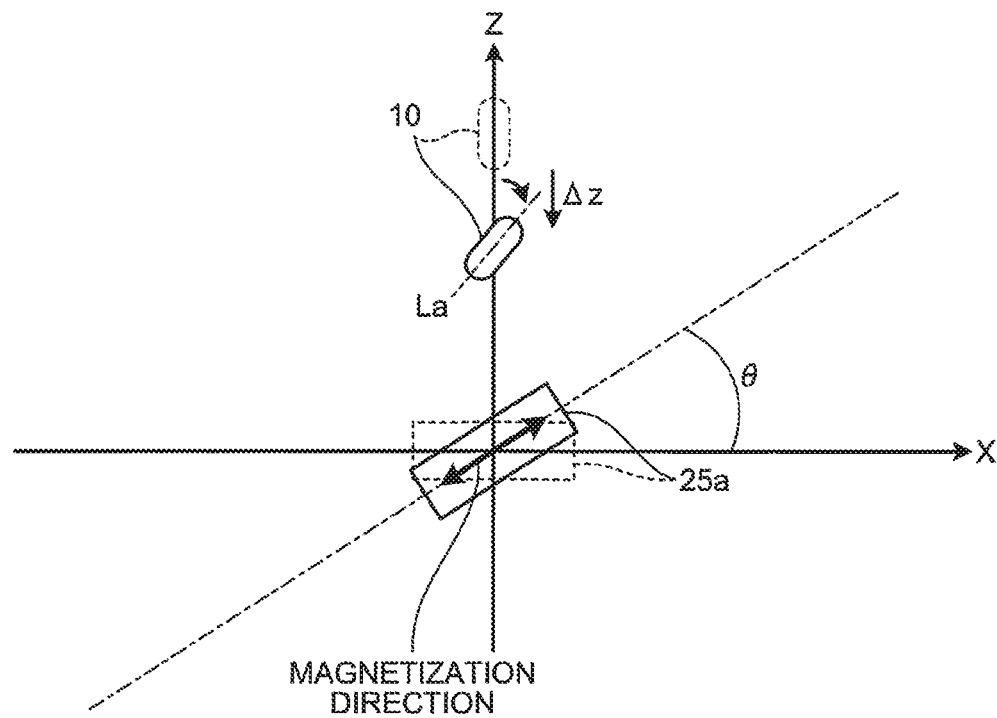
FIG. 15 is a conceptual diagram illustrating the principle of correction of the vertical magnetic attracting force generated in the capsule endoscope.

For example, in FIG. 14, when the extracorporeal permanent magnet 25a is rotated to have an angle θ between the magnetization direction and the X axis, a magnetic field distribution is changed in a space including the position of the capsule endoscope 10. At this time, as described above, since the capsule endoscope 10 is restrained at a position having a minimum vertical magnetic attracting force of the extracorporeal permanent magnet 25a, at first, when the extracorporeal permanent magnet 25a is rotated, the vertical magnetic attracting force gradually increases at the position of the capsule endoscope 10. Accordingly, the capsule endoscope 10 is strongly attracted toward the extracorporeal permanent magnet 25a, and the position of the capsule endoscope 10 is moved along the Z axis, as illustrated in FIG. 15, despite user's intention of only changing the posture of the capsule endoscope 10 without changing the position thereof.

Figure 16:
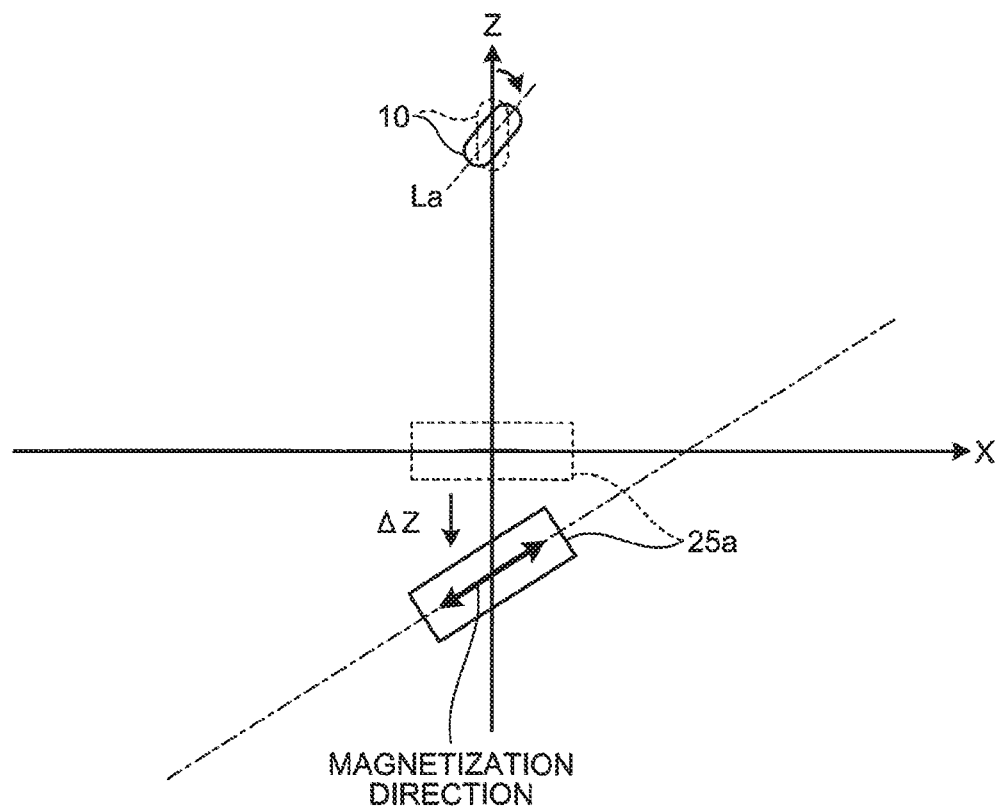
FIG. 16 is a conceptual diagram illustrating the principle of correction of the vertical magnetic attracting force generated in the capsule endoscope.

Therefore, in order to maintain the capsule endoscope 10 at the user's desired position, the control unit 26 moves the extracorporeal permanent magnet 25a along the Z axis by a distance corresponding to a distance ΔZ to be used to adjust an amount of change of the vertical magnetic attracting force generated in the capsule endoscope 10 which is caused by the rotation of the extracorporeal permanent magnet 25a, as illustrated in FIG. 16. Therefore, the change in magnetic attracting force at the position of the capsule endoscope 10 is restricted to prevent unexpected displacement of the capsule endoscope 10.

Figure 17:
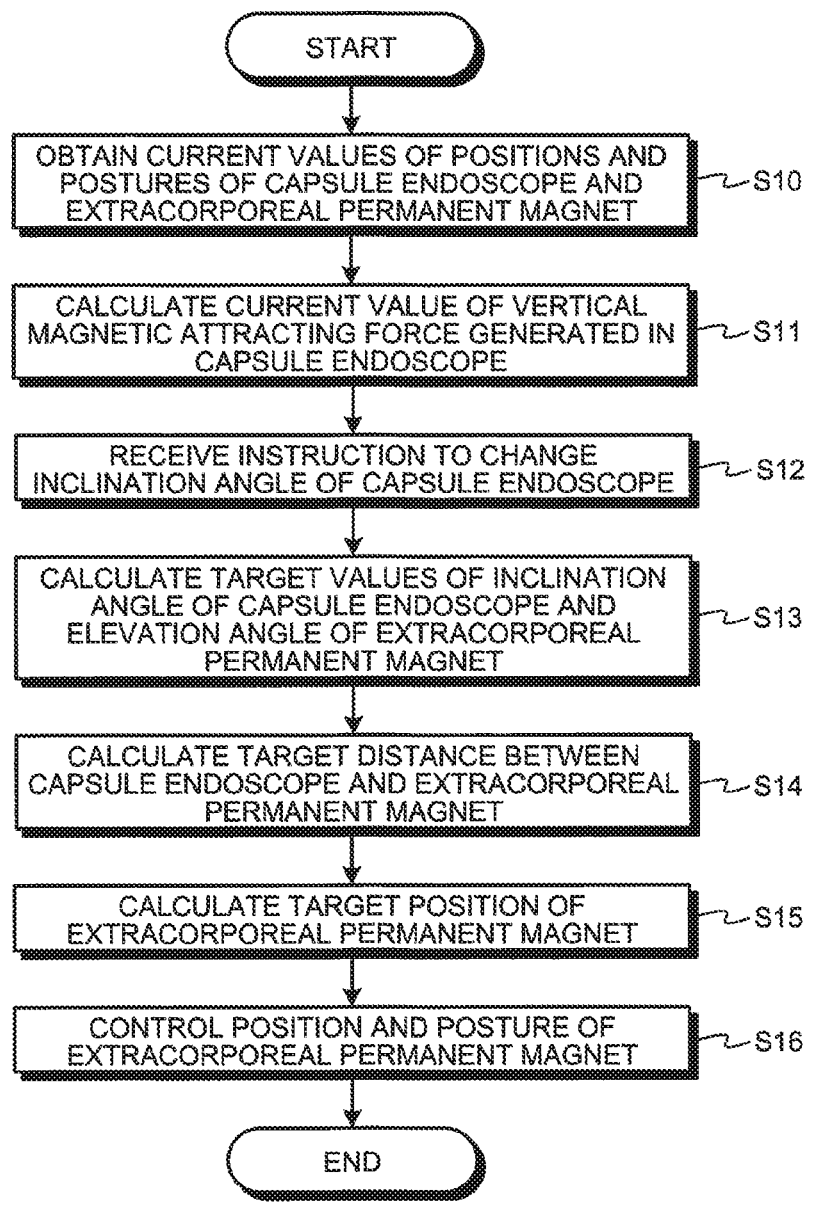
FIG. 17 is a flowchart illustrating correction of the vertical magnetic attracting force generated in the capsule endoscope by a control unit.

FIG. 17 is a flowchart illustrating correction of the vertical magnetic attracting force generated in the capsule endoscope 10 by a control unit 26 configured as described above.

First, in step S10, the control unit 26 obtains current values of the current position and posture of the capsule endoscope 10, from the position and posture detecting unit 22, and obtains current values of the position and posture of the extracorporeal permanent magnet 25*a* on the basis of current control information for the magnetic field generating unit 25.

In the following step S11, the control unit 26 calculates the position and the posture of the capsule endoscope 10, and a vertical magnetic attracting force generated currently in the capsule endoscope 10 (current value of magnetic attracting force) on the basis of the position and the posture of the extracorporeal permanent magnet 25*a*.

Here, the vertical magnetic attracting force depends on the position and the posture of the capsule endoscope 10 obtained in step S10, and the position and the posture of the extracorporeal permanent magnet 25*a*. Therefore, in the present first embodiment, a calculation formula for magnetic attracting force is previously stored in the storage unit 27. In the calculation formula, the position and the posture of the capsule endoscope 10, and the position and the posture of the extracorporeal permanent magnet 25*a* are defined as variables. The control unit 26 uses this calculation formula to obtain the magnetic attracting force.

Alternatively, instead of the calculation formula, the storage unit 27 may previously store a calculation table in which the position and the posture of the capsule endoscope 10, the position and the posture of the extracorporeal permanent magnet 25*a*, and the vertical magnetic attracting force are associated with each other. In this configuration, the control unit 26 uses this calculation table to obtain the magnetic attracting force.

Then, in the following step S12, the control unit 26 receives an instruction to change an inclination angle of the major axis La of the capsule endoscope 10 relative to the vertical direction (see FIG. 7) (hereinafter, simply referred to as inclination angle), on the basis of the guidance instruction information input from the operation input unit 24.

In the following step S13, the control unit 26 calculates a target value of the inclination angle of the capsule endoscope 10, and a target value of the elevation angle of the extracorporeal permanent magnet 25*a* on the basis of the current inclination angle of the capsule endoscope 10 and the instruction for changing the inclination angle.

In the following step S14, on condition that the capsule endoscope 10 and the extracorporeal permanent magnet 25*a* are located at the current positions, the control unit 26 calculates a target distance between the capsule endoscope 10 and the extracorporeal permanent magnet 25*a* in the vertical direction so that when the inclination angle of the capsule endoscope 10 and the elevation angle of the extracorporeal permanent magnet 25*a* are set to the target values of the respective angles, a magnetic attracting force to be generated in the capsule endoscope 10 is equal to a magnetic attracting force currently being generated in the capsule endoscope 10.

Here, a target distance of the extracorporeal permanent magnet 25*a* in the vertical direction can be calculated using an inverse function of the calculation formula, or an inverse conversion table of the calculation table used in step S11. In the calculation formula or the calculation table, since the vertical magnetic attracting force generated in the capsule endoscope 10 is increased, with increasing inclination angle of the capsule endoscope 10 and elevation angle of the extracorporeal permanent magnet 25*a* (with increasing angle relative to the vertical axis), the target distance calculated in the step S14 is increased with increasing inclination angle of the capsule endoscope 10 and elevation angle of the extracorporeal permanent magnet 25*a*.

In the following step S15, the control unit 26 calculates a target position of the extracorporeal permanent magnet 25*a* in the vertical direction, from the current value of the position of the capsule endoscope 10 in the vertical direction, and the target distance between the capsule endoscope 10 and the extracorporeal permanent magnet 25*a* in the vertical direction.

In the following step S16, the control unit 26 controls the operation of the vertical position changing unit 25*c* and the elevation angle changing unit 25*d*, on the basis of the target value of the elevation angle of the extracorporeal permanent magnet 25*a* calculated in step S13, and the target position of the extracorporeal permanent magnet 25*a* in the vertical direction calculated in step S15, and controls the position and the posture of the extracorporeal permanent magnet 25*a*. Thus, the inclination angle of the capsule endoscope 10 can be changed, while maintaining the magnetic attracting force to be generated in the capsule endoscope 10 constant, and the capsule endoscope 10 can be changed to a user's desired posture at the user's desired position.

Here, when the guidance instruction information input from the operation input unit 24 includes information about operation for translating the capsule endoscope 10 in the vertical direction, the control unit 26 calculates a target distance in consideration of a magnetic attracting force required to move the capsule endoscope 10 to a user's desired vertical position, for the magnetic attracting force currently being generated in the capsule endoscope 10, in step S14.

Note that, the guidance instruction information includes information about operation for translating the capsule endoscope 10 in the horizontal direction, or information about the azimuth angle changing operation, the control unit 26 controls at least one of the first plane position changing unit 25*b* and the turn angle changing unit 25*e*, together with the vertical position changing unit 25*c* and the elevation angle changing unit 25*d*, on the bases of these information, and causes the capsule endoscope 10 to perform at least one of translation and turning.

Here, when the rotation speed of the extracorporeal permanent magnet 25*a* is too fast, the capsule endoscope 10 cannot follow the change in magnetic field, and the capsule endoscope 10 may have an unstable posture. Furthermore, it is difficult to increase the movement speed for moving the extracorporeal permanent magnet 25*a* along the vertical direction, due to inertial force. Thus, an upper limit value may be previously set to the rotation speed or the movement speed of the extracorporeal permanent magnet 25*a*. In this configuration, when the rotation speed or the movement speed of the extracorporeal permanent magnet 25*a* based on operation instruction information input from the operation input unit 24 exceeds the upper limit value, due to quick user's operation of the operation input unit 24, the control unit 26 preferably rotates and moves the extracorporeal permanent magnet 25*a* with the upper limit value.

Alternatively, the control unit 26 may have upper limit values of rotational acceleration and movement acceleration of the extracorporeal permanent magnet 25*a*, instead of the rotation speed and the movement speed to control the rotational acceleration and movement acceleration not to exceed the upper limit values.

Furthermore, when the extracorporeal permanent magnet 25a is rotated or moved on the basis of the operation instruction information input from the operation input unit 24, the control unit 26 may prevent the extracorporeal permanent magnet 25a from being operated on the basis of new operation instruction information, before movement of the capsule endoscope 10 generated by the rotation or the movement of the extracorporeal permanent magnet 25a is stopped. That is, when certain operation instruction information is input, and then next operation instruction information is input, the control unit 26 determines whether the movement of the capsule endoscope 10 is stopped which is caused by the operation of the extracorporeal permanent magnet 25a based on the preceding operation instruction information, and upon determination that the movement of the capsule endoscope 10 is stopped, the control unit 26 starts the operation of the extracorporeal permanent magnet 25a on the basis of the next operation instruction information. The determination may be made whether the movement of the capsule endoscope 10 is stopped, for example, after a predetermined time period has elapsed since the operation of the extracorporeal permanent magnet 25a performed on the basis of the preceding operation instruction information. Alternatively, the determination whether the movement of the capsule endoscope 10 is stopped may be made, on the basis of the positional information and the posture information output from the position and posture detecting unit 22.

As described above, according to the present first embodiment, correction of the change in vertical magnetic attracting force generated in the capsule endoscope 10, which is caused by the rotation of the extracorporeal permanent magnet 25a, allows control of the capsule endoscope 10 to have the user's desired posture while maintaining stability of the position of the capsule endoscope.

Note that, the position and posture detecting unit 22 may estimate the posture (azimuth angle and inclination angle) of the capsule endoscope 10, by predicting the magnetic field generated in the vicinity of the capsule endoscope 10 by the extracorporeal permanent magnet 25a, on the basis of a relative positional relationship between the capsule endoscope 10 and the extracorporeal permanent magnet 25a, and the posture of the extracorporeal permanent magnet 25a. Since a result of detection of the position and the posture of the capsule endoscope 10 based on a strength of the wireless signal transmitted from the capsule endoscope 10 commonly includes a noise component, a series of operation illustrated in FIG. 17, which is performed on the basis of the current value of the position and posture of the capsule endoscope 10 detected as described above, may provide unstable control. In contrast, as described above, the extracorporeal permanent magnet 25a predicts the magnetic field generated in the vicinity of the capsule endoscope 10, and estimates the posture of the capsule endoscope 10, and a series of operation illustrated in FIG. 17 can be performed on the basis of a result of the estimation. Thus, influence of the noise can be eliminated and more stable user's desired control can be achieved.

Furthermore, in the fluid W, the position of the capsule endoscope 10 in the horizontal direction is restrained at a specific position relative to the extracorporeal permanent magnet 25a, as illustrated in FIG. 9. Therefore, the position and posture detecting unit 22 may estimate the position of the capsule endoscope 10 in the horizontal direction, on the basis of the positions of the capsule endoscope 10 and the extracorporeal permanent magnet 25a in the vertical direction, and the posture of the extracorporeal permanent magnet 25a. This configuration can also eliminate the influence of the noise included in the result of the detection in comparison with detection of the position of the capsule endoscope 10 in the horizontal direction based on the wireless signal transmitted from the capsule endoscope 10, and thus, more stable user's desired control can be achieved.

Modification 1-1

Next, Modification 1-1 of the present first embodiment will be described. The guidance device 20 may previously define a relative displacement amount of the extracorporeal permanent magnet 25a to maintain the magnetic attracting force of the extracorporeal permanent magnet 25a in the vertical direction constant, upon changing the elevation angle of the extracorporeal permanent magnet 25a. In this configuration, even if the position information and the posture information of the capsule endoscope 10 cannot be obtained, the control unit 26 can control the vertical position changing unit 25c, on the basis of the relative displacement amount previously defined, according to the amount of change in elevation angle of the extracorporeal permanent magnet 25a based on the operation instruction information.

Modification 1-2

Next, Modification 1-2 of the present first embodiment will be described. The guidance device 20 may include at least two guidance modes being guidance modes selectable by the user for guiding the capsule endoscope 10. In this configuration, for example, the display unit 23 displays a plurality of choices representing the guidance modes for the capsule endoscope 10, on the screen, under the control of the control unit 26.

For example, the guidance modes selectable by the user include the following (a) to (c):

(a) a mode for guiding the capsule endoscope 10 in which the capsule endoscope 10 is attracted vertically downward to be in contact with for example an intestinal wall;

(b) a mode for guiding the capsule endoscope 10 in which the capsule endoscope 10 is attracted vertically upward to be in contact with for example the intestinal wall or the fluid surface; and (c) a mode for floating the capsule endoscope 10 in which the capsule endoscope 10 is not brought into contact with the intestinal wall or the fluid surface.

The operation input unit 24 receives a selection signal representing selection of one of the plurality of choices by user's operation, and inputs the selection signal to the control unit 26. The control unit 26 sets a guidance mode corresponding to the input selection signal as a current guidance mode, and controls the magnetic field generating unit 25 to guide the capsule endoscope 10 using the set guidance mode.

When the guidance instruction information is input from the operation input unit 24, the control unit 26 calculates the turn angle, the elevation angle, a translation direction, and a translation amount for controlling the extracorporeal permanent magnet 25a, and obtains the target distance between the capsule endoscope 10 and the extracorporeal permanent magnet 25a in the vertical direction, according to the calculated elevation angle, the posture of the capsule endoscope 10 upon the calculation, and the current guidance mode. This is because the flotation applied to the capsule endoscope 10 is different between a state in which the capsule endoscope 10 is located near a bottom of the fluid (corresponding to (a) described above), a state in which the capsule endoscope 10 is located near the fluid surface (corresponding to (b) described above), and a state in which the capsule endoscope 10 floats in the fluid (corresponding to (c) described above), and thus, a difference occurs in influence of the change in magnetic attracting force caused by the rotation of the extracorporeal permanent magnet 25a. Therefore, in consideration of these states of the capsule endoscope 10, the control unit 26 obtains the target distance to perform control of the magnetic field generating unit 25 to correct the vertical magnetic attracting force generated in the capsule endoscope 10.

Modification 1-3

Next, Modification 1-3 of the present first embodiment will be described. A front view of the operation input unit 24 according to Modification 1-3 is illustrated in (a) of FIG. 18, a right side view of the operation input unit 24 is illustrated in (b) of FIG. 18, and FIG. 19 is a diagram illustrating another example of the contents of operation of the capsule endoscope 10 designated by operating the component units of the operation input unit 24.

The operations of the operation input unit 24 and the guidance operation of the capsule endoscope 10 may be associated with each other to guide the capsule endoscope 10 along not the horizontal plane Hp but an orthogonal plane to the major axis La of the capsule endoscope 10, as described below. Hereinafter, the movement of the capsule endoscope 10 will be described, which corresponds to guidance operation of the capsule endoscope 10 guided along the orthogonal plane to the major axis La of the capsule endoscope 10.

As illustrated in (a) of FIG. 18, up-and-down tilting directions of the joystick 32 indicated by an arrow Y23j designate down guidance directions or up guidance directions in which the capsule endoscope 10 moves in the orthogonal plane to the major axis La as indicated by an arrow Y23, as illustrated in FIG. 19. When operation information corresponding to the tilting operation of the joystick 32 indicated by the arrow Y23j is input from the operation input unit 24 to the control unit 26, the magnetic field generating unit 25 calculates a guidance direction and a guidance amount of the distal end of the capsule endoscope 10 on the absolute coordinate system, corresponding to the tilting direction of the joystick 32, on the basis of the operation information, and controls the first plane position changing unit 25b and the vertical position changing unit 25c to translate the extracorporeal permanent magnet 25a, according to the calculated guidance direction and guidance amount.

As illustrated in (a) of FIG. 18, right-and-left tilting directions of the joystick 32 indicated by an arrow Y24j designate a right guidance direction or a left guidance direction in which the capsule endoscope 10 moves in the orthogonal plane to the major axis La as indicated by an arrow Y24, as illustrated in FIG. 19. When operation information corresponding to tilting operation of the joystick 32 indicated by the arrow Y24j is input from the operation input unit 24 to the control unit 26, the control unit 26 calculates the guidance direction and the guidance amount of the distal end of the capsule endoscope 10 on the absolute coordinate system, corresponding to the tilting direction of the joystick 32, on the basis of the control information, and controls the first plane position changing unit 25b to translate the extracorporeal permanent magnet 25a, according to the calculated guidance direction and guidance amount.

As illustrated in (b) of FIG. 18, pressing of the up button 34U or the down button 34B as indicated by arrows Y25j and Y26j designates a forward guidance direction or a backward guidance direction in which the capsule endoscope 10 moves forward and backward relative to the imaging elements 14A and 14B, along the major axis La, as indicated by arrows Y25 and Y26, as illustrated in FIG. 19. When the operation information corresponding to pressing operation of the up button 34U or the down button 34B indicated by the arrows Y25j and Y26j is input from the operation input unit 24 to the control unit 26, the control unit 26 calculates the guidance direction and the guidance amount of the distal end of the capsule endoscope 10 on the absolute coordinate system, corresponding to pressing of any of the buttons on the basis of the operation information, and controls the first plane position changing unit 25b and the vertical position changing unit 25c to translate the extracorporeal permanent magnet 25a, according to the calculated guidance direction and guidance amount.

As illustrated in (a) of FIG. 18, up-and-down tilting directions of the joystick 31 indicated by an arrow Y21j corresponds to a tilting guidance direction in which the distal end of the capsule endoscope 10 swings to pass through the vertical axis Az, as indicated by an arrow Y21 of FIG. 19, and right-and-left tilting directions of the joystick 31 indicated by an arrow Y22j corresponds to a rotation guidance direction in which the capsule endoscope 10 rotates about the axis Az, as indicated by an arrow Y22 of FIG. 19.

Modification 1-4

Next, Modification 1-4 of the present first embodiment will be described. For a method of detecting the position of the capsule endoscope 10 in the subject, a method of detecting an alternating magnetic field may be employed. In this configuration, an alternating magnetic field generation unit for generating the alternating magnetic field is provided in the capsule endoscope 10. In contrast, the guidance device 20 is provided with a plurality of magnetic field sensors for detecting an alternating magnetic field.

The guidance device 20 detects the alternating magnetic field generated by the capsule endoscope 10 using a plurality of magnetic field sensors positioned at a plurality of locations to continuously calculate at least one of the position and the direction of the capsule endoscope 10 on the basis of these results of the detection.

Modification 1-5

Next, Modification 1-5 of the present first embodiment will be described. For a method of detecting the position of the capsule endoscope 10 in the subject, another method of detecting the alternating magnetic field will be described. In this configuration, an LC circuit resonated by the alternating magnetic field is provided in the capsule endoscope 10. In addition, the guidance device 20 is provided with a plurality of magnetic field sensors for detecting the alternating magnetic field.

When the capsule endoscope 10 is not positioned in a measurement area of the subject (area of the magnetic field formed by the magnetic field generating unit 25), the guidance device 20 previously detects a first resonance magnetic field generated by the LC circuit in the capsule endoscope 10. Then, when the capsule endoscope 10 is positioned in the measurement area in the subject, a second resonance magnetic field generated by the LC circuit in the capsule endoscope 10 is detected to continuously determine difference values between the detected value of the first resonance magnetic field and the detected value of the second resonance magnetic field. Furthermore, on the basis of these difference values, positional coordinates of the capsule endoscope 10 in a three-dimensional space are continuously calculated.

Modification 1-6

Figure 20:
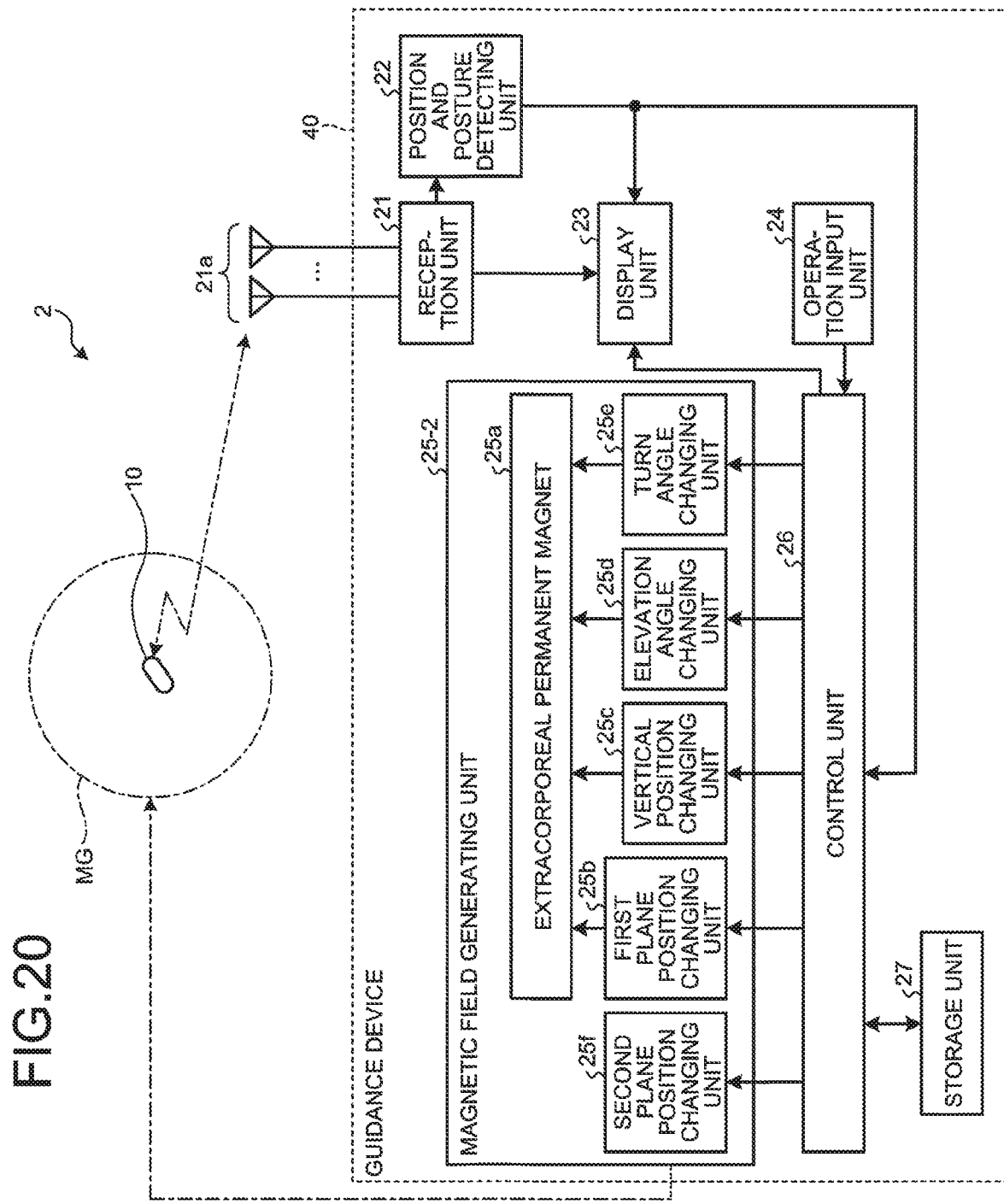
FIG. 20 is a diagram illustrating an exemplary configuration of a capsule medical device guidance system according to Modification 1-6 of the first embodiment.

Next, Modification 1-6 of the present first embodiment will be described. FIG. 20 is a diagram illustrating an exemplary configuration of a capsule medical device guidance system according to Modification 1-6. As illustrated in FIG. 20, a capsule medical device guidance system 2 according to Modification 1-6 includes a guidance device 40 having a magnetic field generating unit 25-2, instead of the guidance device 20 illustrated in FIG. 1. The magnetic field generating unit 25-2 further includes a second plane position changing unit 25*f* to the magnetic field generating unit 25 illustrated in FIG. 1. Note that, configurations other than the second plane position changing unit 25*f* in the capsule medical device guidance system 2 are similar to those described in the present first embodiment.

Figure 21:
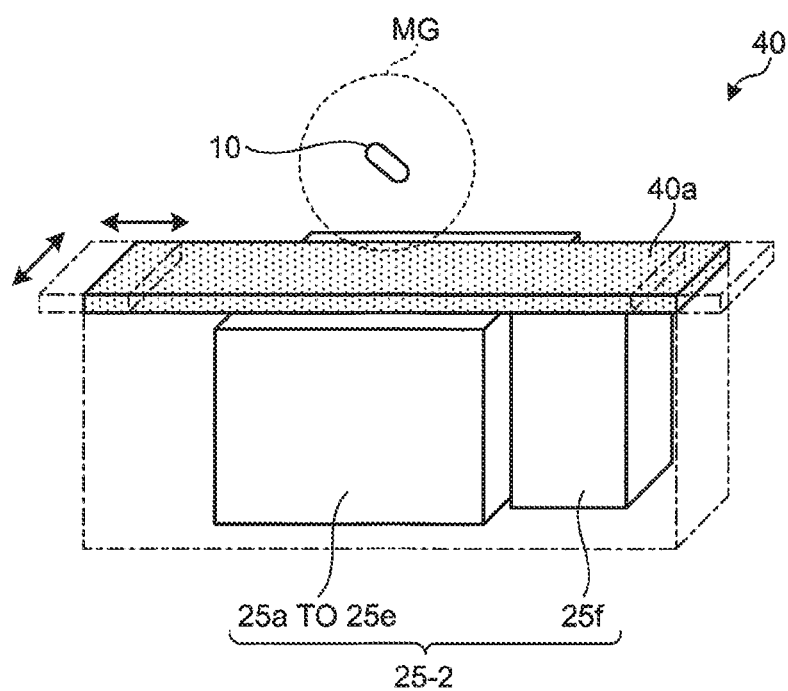
FIG. 21 is a schematic perspective view of an example of appearance of a guidance device illustrated in FIG. 20.

FIG. 21 is a schematic perspective view of an example of appearance of the guidance device 40. As illustrated in FIG. 21, the guidance device 40 is provided with a bed 40*a* translated in a horizontal direction as a mounting stage on which the subject is mounted. Under the bed 40*a*, the magnetic field generating unit 25-2 generating the magnetic field MG is disposed.

The second plane position changing unit 25*f* is a translation mechanism translating the bed 40*a* in the horizontal direction. The second plane position changing unit 25*f* moves the bed 40*a* on which the subject is mounted to change a position of the subject relative to the capsule endoscope 10 restrained in the magnetic field MG generated by the extracorporeal permanent magnet 25*a*, in other words, a position of the capsule endoscope 10 relative to the subject.

Second Embodiment

Figure 22:
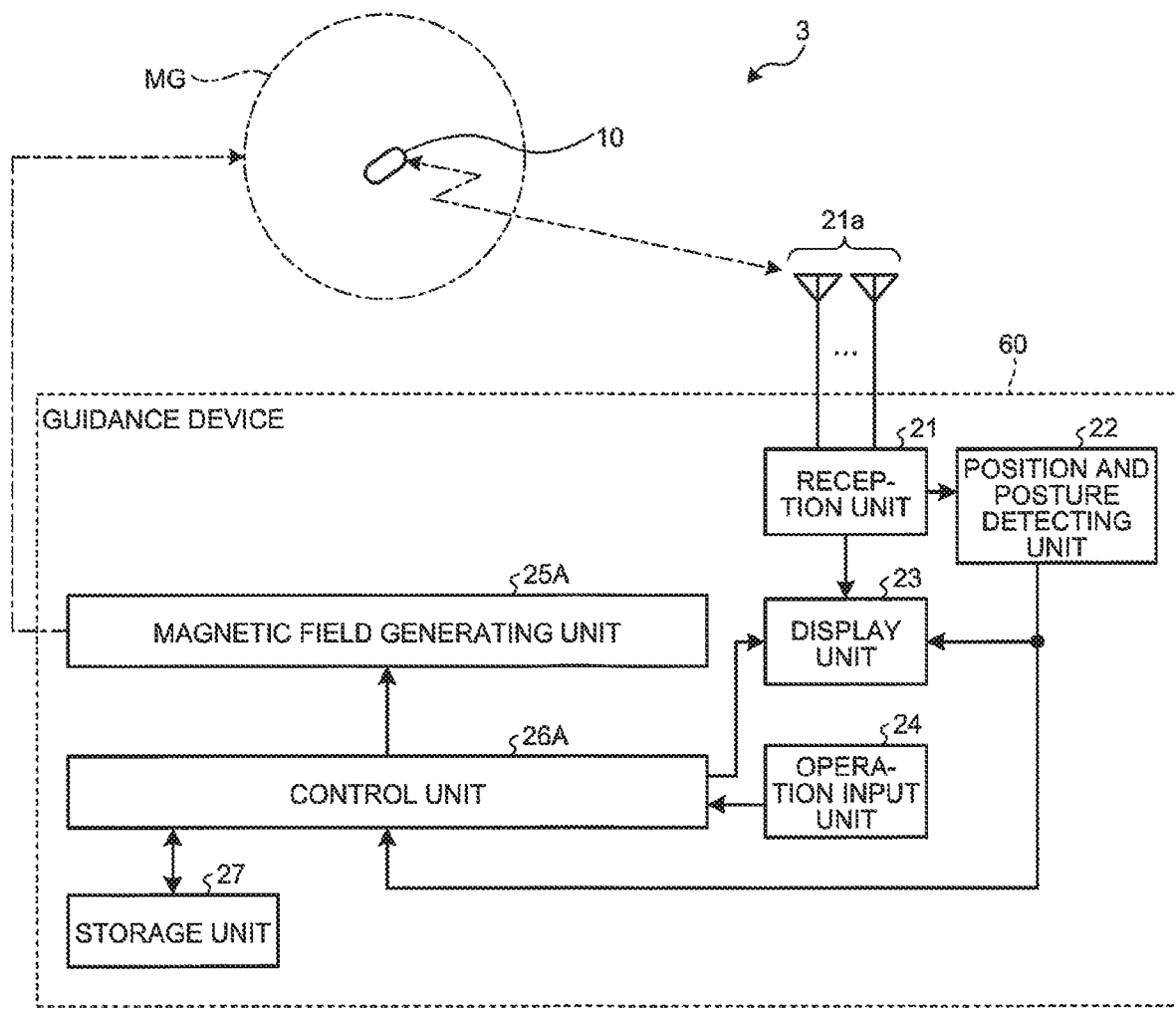
FIG. 22 is a diagram illustrating an exemplary configuration of a capsule medical device guidance system according to a second embodiment of the disclosure.
Figure 23:
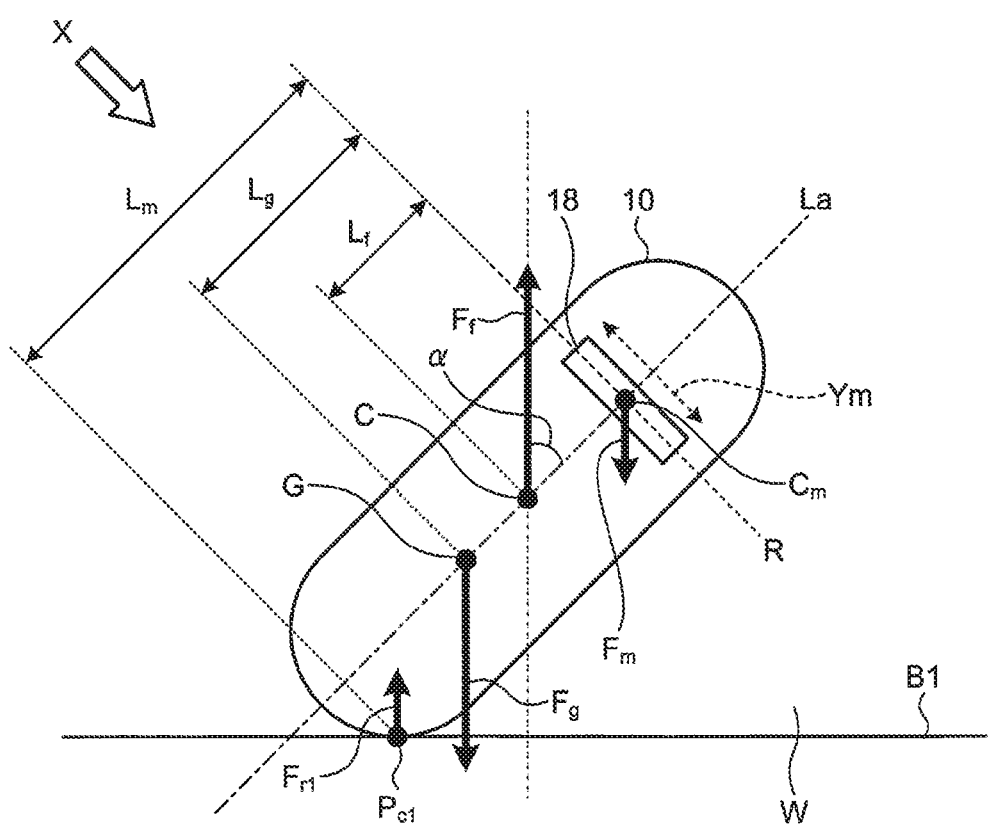
FIG. 23 is a schematic view illustrating a state in which the capsule endoscope makes contact with a lower boundary surface in the subject into which fluid is introduced.

FIG. 22 is a schematic view illustrating an exemplary configuration of a capsule medical device guidance system according to a second embodiment of the disclosure. As illustrated in FIG. 23, a capsule medical device guidance system 3 according to the second embodiment includes the capsule endoscope 10 being a capsule medical device introduced into the body cavity of the subject and internally provided with the permanent magnet as the first magnet, and a guidance device 60 generating the magnetic field MG to magnetically guiding the capsule endoscope 10 introduced into the subject.

The guidance device 60 includes the reception unit 21, the position and posture detecting unit 22, the display unit 23, the operation input unit 24, a magnetic field generating unit 25A, a control unit 26A, and a storage unit 27. The reception unit 21 performs wireless communication with the capsule endoscope 10 to receive a wireless signal including the image information obtained by the capsule endoscope 10, the position and posture detecting unit 22 detects a position and a posture of the capsule endoscope 10 in the subject, on the basis of the wireless signal received from the capsule endoscope 10, the display unit 23 obtains the image information from the wireless signal received by the reception unit 21, performs predetermined signal processing on the image information to display an in-vivo image on a screen, and displays the position of the capsule endoscope 10 in the subject, on the screen, the operation input unit 24 receives, for example, input information directing various operations in the capsule medical device guidance system 3, the magnetic field generating unit 25A generates a magnetic field for guiding the capsule endoscope 10, the control unit 26A controls these units, and the storage unit 27 stores the image information or the like captured by the capsule endoscope 10.

The guidance device 60 is provided with the bed 20*a* illustrated in FIG. 2, as a mounting stage on which the subject is mounted. Under the bed 20*a*, at least the magnetic field generating unit 25A generating the magnetic field MG is disposed.

The magnetic field generating unit 25A generates a magnetic field for changing the position, the inclination angle, and the azimuth angle of the capsule endoscope 10 introduced into the subject, relative to the subject. A configuration of the magnetic field generating unit 25A is not particularly limited, as long as the magnetic field MG in which the magnetic gradient can be controlled by the control unit 26A can be formed on an area over the bed 20*a* on which the subject is mounted. For example, the magnetic field generating unit 25A may include an electromagnet, or the extracorporeal permanent magnet and a drive unit changing a position or a direction of the extracorporeal permanent magnet.

The control unit 26A controls the magnetic field generating unit 25A on the basis of a detection result from the position and posture detecting unit 22, and guidance instruction information received by the operation input unit 24, and guides the capsule endoscope 10 to a user's desired position and posture.

Next, a specific configuration and operation of the operation input unit 24 will be described. The guidance instruction information corresponding to the tilting operation of the joystick 31 indicated by the arrow Y11*j* in (a) of FIG. 11, is input from the operation input unit 24 to the control unit 26A, the control unit 26A calculates a guidance direction of the distal end of the capsule endoscope 10 on the absolute coordinate system corresponding to a tilting direction of the joystick 31, on the basis of this guidance instruction information, and calculates a guidance amount corresponding to the tilting operation of the joystick 31. Then, the magnetic field generating unit 25A is controlled to generate a magnetic field having a magnetic orientation changed according to the calculated guidance direction and guidance amount.

The guidance instruction information corresponding to the tilting operation of the joystick 31 indicated by the arrow Y12*j* in (a) of FIG. 11, is input from the operation input unit 24 to the control unit 26A, the control unit 26A calculates a guidance direction of the distal end of the capsule endoscope 10 on the absolute coordinate system corresponding to the tilting direction of the joystick 31, on the basis of this guidance instruction information, and calculates the guidance amount corresponding to the tilting operation of the joystick 31, and controls the magnetic field generating unit 25A to generate a magnetic field having a magnetic orientation changed according to the calculated guidance direction and the guidance amount.

When the guidance instruction information corresponding to the tilting operation of the joystick 32 indicated by the arrow Y13*j* in (a) of FIG. 11 is input from the operation input unit 24 to the control unit 26A, the control unit 26A calculates the guidance direction and the guidance amount of the distal end of the capsule endoscope 10 on the absolute coordinate system corresponding to the tilting direction of the joystick 32, on the basis of the guidance instruction information, and controls the magnetic field generating unit 25A to generate a magnetic field having a magnetic gradient changed according to the calculated guidance direction and the guidance amount.

When the guidance instruction information corresponding to the tilting operation of the joystick 32 indicated by the arrow Y14j illustrated in (a) of FIG. 11 is input from the operation input unit 24 to the control unit 26A, the control unit 26A calculates the guidance direction and the guidance amount of the distal end of the capsule endoscope 10 on the absolute coordinate system corresponding to the tilting direction of the joystick 32, on the basis of this guidance instruction information. In response to the calculation, the magnetic field generating unit 25A generates the magnetic field having a magnetic gradient changed, according to the guidance direction and the guidance amount calculated by the control unit 26A.

When the guidance instruction information corresponding to the pressing operation of the up button 34U or the down button 34B indicated by the arrow Y15j or Y16j in (b) of FIG. 11 is input from the operation input unit 24 to the control unit 26A, the control unit 26A calculates the guidance direction and the guidance amount of the distal end of the capsule endoscope 10 on the absolute coordinate system, corresponding to pressing of any of the buttons, on the basis of the guidance instruction information, and controls the magnetic field generating unit 25A to generate a magnetic field having a magnetic gradient changed according to the guidance direction and the guidance amount.

Figure 24:
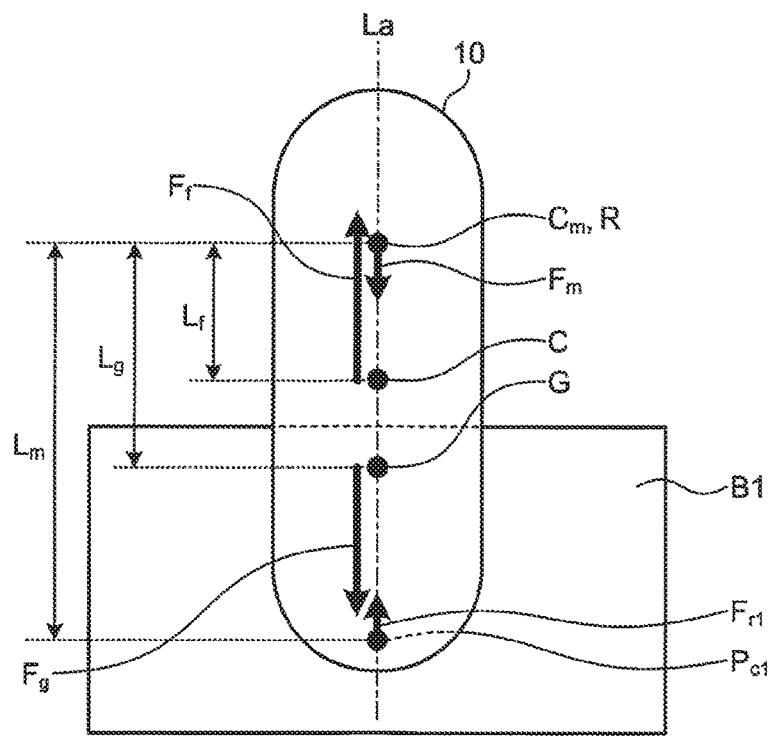
FIG. 24 is a view taken in the direction of an arrow X of FIG. 23.
Figure 25:
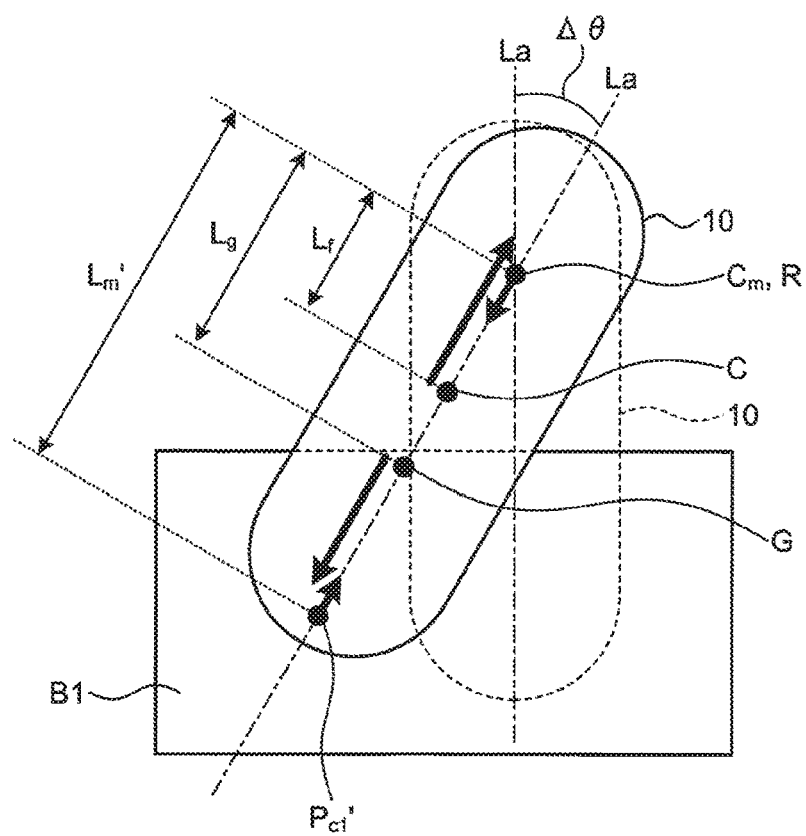
FIG. 25 is a schematic view illustrating a state in which the capsule endoscope illustrated in FIG. 24 is rotated while receiving an external force.

FIG. 23 is a schematic view illustrating a state in which the capsule endoscope 10 positioned in the fluid W makes contact with a lower boundary surface B1 (inner wall surface of organ). Furthermore, FIG. 24 is a view taken in the direction of an arrow X of FIG. 23. FIG. 25 is a schematic view illustrating a state in which the capsule endoscope 10 illustrated in FIG. 24 is rotated while receiving an external force.

As illustrated in FIG. 23, the following forces are applied to respective points of the capsule endoscope 10.

Geometric center C of the capsule endoscope 10: flotation $F_f$

Center of gravity G of the capsule endoscope 10: gravity $F_g$

Geometric center $C_m$ of the permanent magnet 18 (hereinafter, simply referred to center): magnetic attracting force $F_m$ Contact point $P_{c1}$ between the capsule endoscope 10 and the boundary surface B1: Reactive force $F_{r1}$ from the boundary surface B1 ($F_{r1}=F_m F_g-F_f$)

Here, FIG. 23 schematically illustrates a state in which the capsule endoscope 10 makes contact with a stomach wall or intestinal wall, in a plane including the geometric center C and the center of gravity G of the capsule endoscope 10, and the center $C_m$ of the permanent magnet 18, and parallel with the magnetization direction Ym of the permanent magnet 18 (i.e., plane including a vector in the magnetization direction Ym, passing through the center $C_m$ of the permanent magnet 18, and parallel with the drawing in FIG. 23. Hereinafter, referred as plane P).

In the second embodiment, the capsule endoscope 10 has a specific weight smaller than the specific weight of the fluid W, and the capsule endoscope 10 floats in the fluid W when no magnetic attracting force $F_m$ is generated in the capsule endoscope 10. Accordingly, in order to bring the capsule endoscope 10 into contact with the boundary surface B1, a downward (in the same direction as the gravity) magnetic attracting force $F_m$ is generated in the capsule endoscope 10.

At this time, when the magnetic attracting force $F_m$ is increased, the capsule endoscope 10 is suddenly rotated about an axis R passing through the center $C_m$ of the permanent magnet 18 and parallel with the magnetization direction $Y_m$ of the permanent magnet 18, as a rotation axis, at the moment when the magnetic attracting force $F_m$ exceeds an upper limit value. That is, when the capsule endoscope 10 is inclined about the axis R owing to an external force about the axis R, the capsule endoscope 10 falls without being restored to an original posture (state in which the plane P is a vertical plane). Therefore, the control unit 26A calculates the upper limit value of the magnetic attracting force $F_m$ within a range in which the capsule endoscope 10 is not unexpectedly rotated, and controls the magnetic field generating unit 25A to generate a magnetic attracting force $F_m$ within a range less than the upper limit value, in the capsule endoscope 10. Hereinafter, a method of calculating the upper limit value of the magnetic attracting force $F_m$ will be described with reference to FIGS. 24 and 25.

As illustrated in FIG. 24, when the axis R is defined as a rotation center, a distance from the axis R to the center of gravity G is denoted by $L_g$, a distance from the axis R to the geometric center C is denoted by $L_f$, and a distance from the contact point $P_{c1}$ between the capsule endoscope 10 and the boundary surface B1 to the axis R is denoted by $L_m$. In the second embodiment, any of the geometric center C, the center of gravity G, and the contact point $P_{ct}$ is positioned below the axis R, and expressed as $L_f<L_g$.

In this configuration, in order to prevent the rotation (falling due to external force) of the capsule endoscope 10, at least relationships (1) preferably hold for a moment of force about the axis R so that the plane P is returned to the vertical plane under the condition that the external force is removed, after the capsule endoscope 10 is inclined by a fine angle $\Delta\theta$ due to the external force, as illustrated in FIG. 25. In the following formula, a distance $L_m'$ represents a distance between the axis R and a contact point $P_{c1}'$ between the capsule endoscope 10 and the boundary surface B1, upon inclination of the capsule endoscope 10.

$$L_f \times F_f \cdot \cos\alpha \sin\Delta\theta + L_m' \times F_{r1} \cdot \cos\alpha \sin\Delta\theta < L_g \times F_g \cdot \cos\alpha \sin\Delta\theta$$

$$L_f \times F_f \cdot \cos\alpha \sin\Delta\theta + L_m \times F_{r1} \cdot \cos\alpha \sin\Delta\theta < L_g \times F_g \cdot \cos\alpha \sin\Delta\theta$$

$$L_f \times F_f + L_m \times F_{r1} < L_g \times F_g$$

$$L_f \times F_f + L_m \times (F_m + F_g - F_f) < L_g - F_g \quad (1)$$

Here, since the angle $\Delta\theta$ is fine, it is considered $L_m'=L_m$ without problem.

Therefore, the range of the magnetic attracting force $F_m$ is given by the following formula (2).

$$F_m < (L_g \times F_g - L_f \times F_f)/L_m + F_f - F_g \quad (2)$$

Accordingly, the upper limit value $F_{max}$ of the magnetic attracting force $F_m$ is given by the following formula (3).

$$F_{max} = (L_g \times F_g - L_f \times F_f)/L_m + F_f - F_g \quad (3)$$

When the magnetic attracting force $F_m$ is controlled within the range of less than the upper limit value $F_{max}$, the rotation of the capsule endoscope 10 not intended by the user can be prevented to continue stable control of the posture of the capsule endoscope 10.

Values expressed in formula (3) includes flotation $F_f$ which is a parameter given by the specific weights of the capsule endoscope 10 and the fluid W, and a volume of the capsule endoscope 10. The gravity $F_g$ and the distances $L_g$ and $L_f$ are parameters determined depending on design of the capsule endoscope 10. Furthermore, the distance $L_m$ may be determined according to the posture of the capsule endoscope 10 (inclination angle α of the major axis La relative to the vertical axis), and may be determined using a maximum value of $L_m$ defined according to a shape of an outside surface of the capsule endoscope 10 (condition of minimum value of $F_m$). At this time, in a distance between the axis R and an arbitrary point on the outside surface of the capsule endoscope 10, when a direction of the center of gravity G is set as positive relative to the geometric center C of the capsule endoscope 10, a maximum value of the distance is preferably adopted as the maximum value of the distance $L_m$.

The control unit 26A calculates the upper limit value $F_{max}$ of the magnetic attracting force $F_m$ given by formula (3), on the basis of the posture of the capsule endoscope 10 detected by the position and posture detecting unit 22. Alternatively, upper limit values $F_{max}$ may be previously stored in the storage unit 27 according to the postures of the capsule endoscope 10 so that a corresponding upper limit value $F_{max}$ is read from the storage unit 27 on the basis of a posture of the capsule endoscope 10 detected by the position and posture detecting unit 22.

Alternatively, the control unit 26A may previously store, in the storage unit 27, the upper limit value $F_{max}$ of the magnetic attracting force $F_m$ given by formula (3) or a value smaller than the upper limit value $F_{max}$ on the basis of the maximum value of the distance $L_m$ defined according to the shape of the outside surface of the capsule endoscope 10, to control the magnetic field generating unit 25A so that the vertical magnetic attracting force $F_m$ does not exceed the stored value.

Furthermore, the control unit 26A may convert the upper limit value $F_{max}$ of the magnetic attracting force $F_m$ to vertical magnetic gradient, on the basis of not the upper limit value $F_{max}$ of the magnetic attracting force $F_m$ but a magnetic moment of the permanent magnet 18 provided in the capsule endoscope 10 to control the magnetic field generating unit 25A on the basis of the value obtained by the conversion so that vertical magnetic gradient generated by the magnetic field generating unit 25A does not exceed the vertical magnetic gradient corresponding to the upper limit value $F_{max}$ of the magnetic attracting force $F_m$.

In JP 2010-17554 A described above, a technology is disclosed in which a fluid such as water is introduced into a subject's digestive tract (e.g., stomach) to guide a capsule endoscope in the fluid. In JP 2010-17554 A, the capsule endoscope having a center of gravity shifted from a geometric center in a direction different from a magnetization direction of a permanent magnet is used to perform guidance while uniquely controlling the posture of the capsule endoscope.

When observation is performed in the fluid by the capsule endoscope, partial contact of the capsule endoscope with the boundary surface such as a fluid bottom (e.g., inner wall surface of stomach) or a fluid surface allows stable control of the position or the posture of the capsule endoscope. Specifically, when the capsule endoscope has a specific weight smaller than the specific weight of the fluid, the downward (in the same direction as the gravity) magnetic attracting force is generated in the capsule endoscope so that the capsule endoscope makes contact with the fluid bottom. Furthermore, when the capsule endoscope has a specific weight larger than the specific weight of the fluid, the upward (in the opposite direction of the gravity) magnetic attracting force is generated in the capsule endoscope so that the capsule endoscope makes contact with the fluid surface or the inner wall surface of the stomach positioned above.

However, when an excessive magnetic attracting force is generated in the capsule endoscope at this time, the posture of the capsule endoscope cannot be controlled and falls.

In contrast, according to the second embodiment of the disclosure, even if the guidance is performed while bringing the capsule endoscope 10 into contact with the boundary surface, in the subject into which the fluid W is introduced, application of a magnetic attracting force within the range of less than the upper limit value $F_{max}$ given by formula (3) (magnetic attracting force $F_m$ in downward direction) to the capsule endoscope 10 (permanent magnet 18) prevents unexpected rotation of the capsule endoscope 10, and control of the posture of the capsule endoscope 10 can be maintained stably.

Modification 2-1

Figure 26:
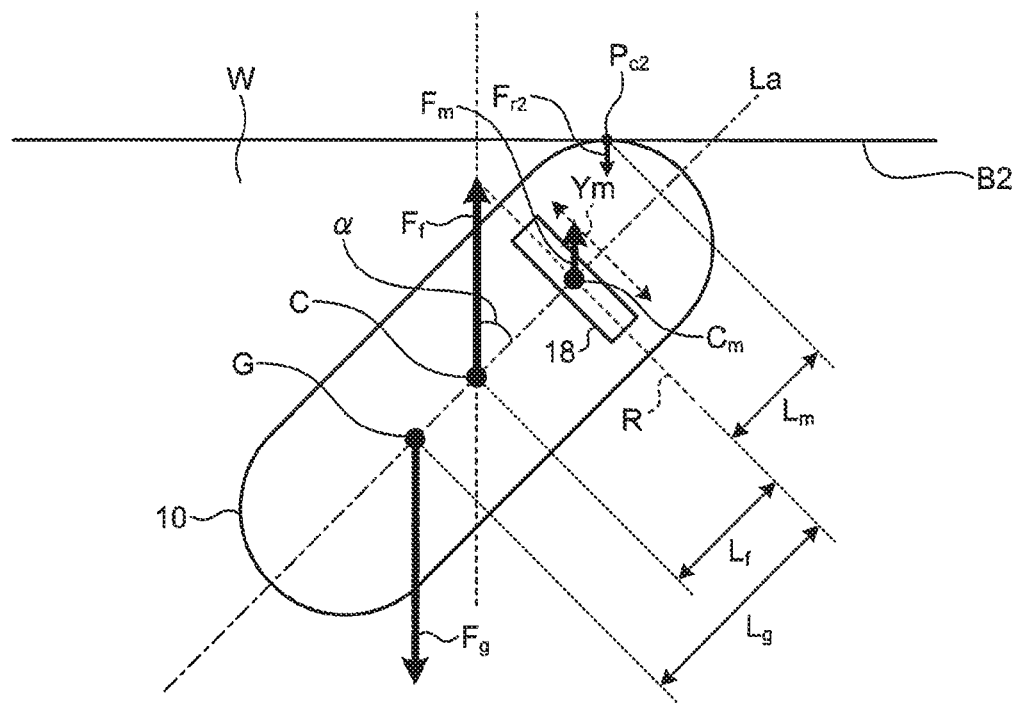
FIG. 26 is a diagram for illustrating a method of calculating an upper limit value of a magnetic attracting force according to Modification 2-1 of the second embodiment.

Next, modification 2-1 of the second embodiment of the disclosure will be described. When the capsule endoscope 10 has a specific weight larger than that of the fluid W, a magnetic attracting force $F_m$ in the opposite direction (upward in FIG. 26) of the gravity may be generated in the capsule endoscope 10, as illustrated in FIG. 26, to control the posture of the capsule endoscope 10 while bringing the capsule endoscope 10 into contact with an upper boundary surface B2 (inner wall surface of organ or fluid surface). At this time, the geometric center C and the center of gravity G are positioned below the axis R, and a contact point $P_{c2}$ is positioned above the axis R. Furthermore, a relationship between the distance $L_g$ from the axis R to the center of gravity G and the distance $L_f$ from the axis R to the geometric center C is expressed as $L_f < L_g$. Furthermore, a reactive force $F_{r2}$ from the boundary surface B2 to the capsule endoscope 10 at the contact point $P_{c2}$ is expressed as $F_{r2} = F_f - F_g + F_m$.

In this configuration, as in the second embodiment, in order to prevent the rotation of the capsule endoscope 10, under the condition that the external force is removed, after the capsule endoscope 10 is inclined by a fine angle Δθ due to the external force about the axis R, relationships (4) preferably hold for the moment of force about the axis R. In the following formula, the distance $L_m'$ represents a distance between the axis R and a contact point $P_{c2}$ between the capsule endoscope 10 and the boundary surface B2, upon inclination of the capsule endoscope 10.

$$L_f \times F_f \cdot \cos\alpha \sin\Delta\theta + L_m' \times F_{r2} \cdot \cos\alpha \sin\Delta\theta < L_g \times F_g \cdot \cos\alpha \sin\Delta\theta$$

$$L_f \times F_f \cos\alpha \sin\Delta\theta + L_m \times F_{r2} \cdot \cos\alpha \sin\Delta\theta < L_g \times F_g \cdot \cos\alpha \sin\Delta\theta$$

$$L_f \times F_f + L_m \times F_{r2} < L_g \times F_g$$

$$L_f \times F_f + L_m \times (F_f - F_g + F_m) < L_g \times F_g \quad (4)$$

Here, since the angle Δθ is fine, it is considered $L_m' = L_m$ without problem.

Therefore, the range of the magnetic attracting force $F_m$ is given by the following formula (5).

$$F_m < (L_g \times F_g - L_f \times F_f)/L_m + F_g - F_f \quad (5)$$

Accordingly, the upper limit value $F_{max}$ of the magnetic attracting force $F_m$ is given by the following formula (6).

$$F_{max}=(L_g \times F_g - L_f \times F_f)/L_m + F_g - F_f \quad (6)$$

The magnetic attracting force $F_m$ is preferably controlled within the range of less than the upper limit value $F_{max}$.

Note that, in the present Modification 2-1, in the distance between the axis R and an arbitrary point on the outside surface of the capsule endoscope 10, when a direction of the geometric center C is set as positive relative to the center of gravity G of the capsule endoscope 10, a value obtained by substituting a maximum value for distance $L_m$ in formula (6) may be used as the upper limit value $F_{max}$ to control the magnetic attracting force $F_m$.

Modification 2-2

Figure 27:
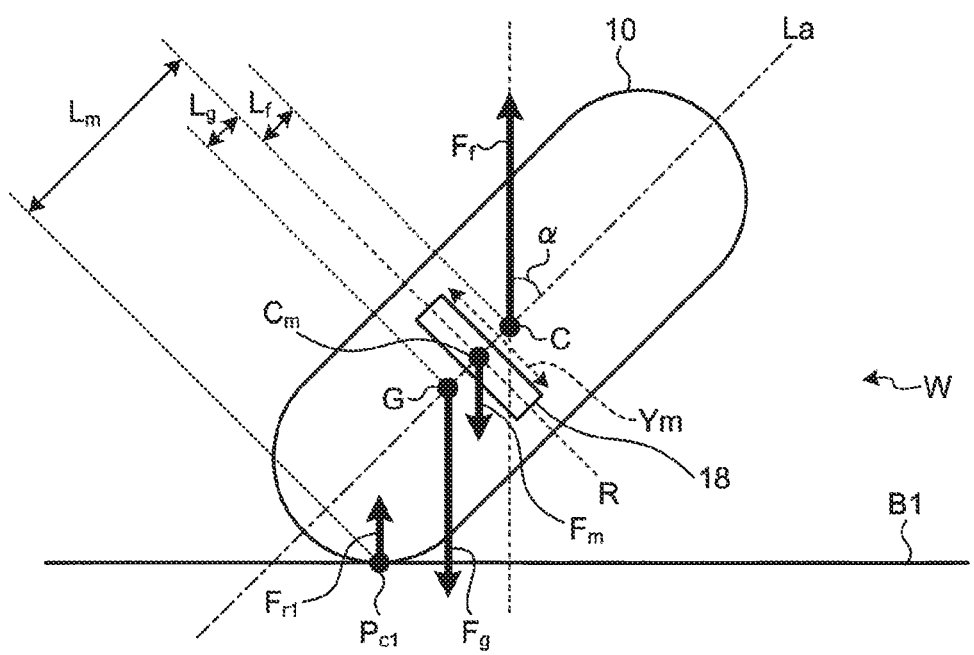
FIG. 27 is a diagram for illustrating a method of calculating an upper limit value of a magnetic attracting force according to Modification 2-2 of the second embodiment.

Next, modification 2-2 of the second embodiment of the disclosure will be described. Disposition of units constituting the capsule endoscope 10 is not limited to that illustrated in FIG. 4. For example, as illustrated in FIG. 27, the center $C_m$ of the permanent magnet 18 may be disposed between the geometric center C and the center of gravity G of the capsule endoscope 10. When the capsule endoscope 10 has a specific weight smaller than that of the fluid W, for control of the posture of the capsule endoscope 10 in contact with the lower boundary surface B1, the upper limit value $F_{max}$ of the magnetic attracting force $F_m$ in the downward direction can be calculated as described below.

In this configuration, the geometric center C is positioned above the axis R, and the center of gravity G and the contact point $P_{c1}$ are positioned below the axis R. Furthermore, the reactive force $F_{r1}$ from the boundary surface B1 to the capsule endoscope 10 at the contact point $P_{c1}$ is expressed as $F_{r1}=F_m+F_g-F_f$.

At this time, as in the second embodiment, in order to prevent the rotation of the capsule endoscope 10, under the condition that the external force is removed, after the capsule endoscope 10 is inclined by a fine angle $\Delta\theta$ due to the external force about the axis R, relationships (7) preferably hold for the moment of force about the axis R. In the following formula, the distance $L_m'$ represents a distance between the axis R and a contact point $P_{c1}$ between the capsule endoscope 10 and the boundary surface B1, upon inclination of the capsule endoscope 10

$L_g \times F_g \cdot \cos \alpha \sin \Delta\theta + L_f \times F_f \cdot \cos \alpha \sin \Delta\theta > L_m' \times F_{r1} \cdot \cos \alpha \sin \Delta\theta$ $L_g \times F_g \cdot \cos \alpha \sin \Delta\theta + L_f \times F_f \cdot \cos \alpha \sin \Delta\theta > L_m \times F_{r1} \cdot \cos \alpha \sin \Delta\theta$ $L_g \times F_g + L_f \times F_f > L_m \times F_{r1}$ $$L_g \times F_g + L_f \times F_f > L_m \times (F_m + F_g - F_f) \quad (7)$$

Here, since the angle $\Delta\theta$ is fine, it is considered $L_m'=L_m$ without problem.

Therefore, the range of the magnetic attracting force $F_m$ is given by the following formula (8).

$$F_m < (L_g \times F_g + L_f \times F_f)/L_m + F_f - F_g \quad (8)$$

Accordingly, $\{(L_g \times F_g + L_f \times F_f)/L_m + F_f - F_g\}$ may be taken as the upper limit value $F_{max}$ of the magnetic attracting force $F_m$ to control the magnetic attracting force $F_m$ within the range of less than this upper limit value $F_{max}$.

Note that, in the present Modification 2-2, in the distance between the axis R and an arbitrary point on the outside surface of the capsule endoscope 10, when the direction of the center of gravity G is set as positive relative to the geometric center C of the capsule endoscope 10, a value obtained by substituting a maximum value for distance $L_m$ in formula (8) may be used as the upper limit value $F_{max}$ to control the magnetic attracting force $F_m$.

Modification 2-3

Figure 28:
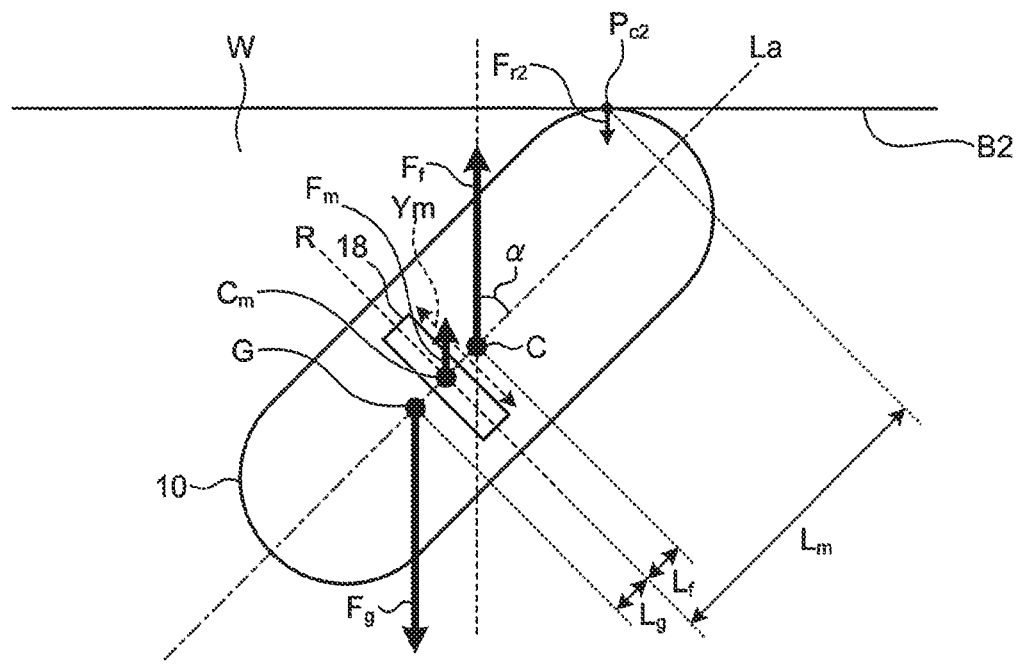
FIG. 28 is a diagram for illustrating a method of calculating an upper limit value of a magnetic attracting force according to Modification 2-3 of the second embodiment.

Next, modification 2-3 of the second embodiment of the disclosure will be described. As illustrated in FIG. 28, in the capsule endoscope 10, when the center $C_m$ of the permanent magnet 18 is disposed between the geometric center C and the center of gravity G, and the capsule endoscope 10 has a specific weight larger than that of the fluid W, for control of the posture of the capsule endoscope 10 while bringing the capsule endoscope 10 into contact with the upper boundary surface B2, an upper limit value $F_{max}$ of the magnetic attracting force $F_m$ in an upward direction is calculated as follows.

In this configuration, the geometric center C and the contact point $P_{c2}$ are positioned above the axis R, and the center of gravity G is positioned below the axis R. Furthermore, the reactive force $F_{r2}$ from the boundary surface B2 to the capsule endoscope 10 at the contact point $P_{c2}$ is expressed as $F_{r2}=F_f-F_g+F_m$.

At this time, as in the second embodiment, in order to prevent the rotation of the capsule endoscope 10, under the condition that the external force is removed, after the capsule endoscope 10 is inclined by a fine angle $\Delta\theta$ due to the external force about the axis R, relationships (9) preferably hold for the moment of force about the axis R. In the following formula, the distance $L_m'$ represents a distance between the axis R and a contact point $P_{c2}$ between the capsule endoscope 10 and the boundary surface B2, upon inclination of the capsule endoscope 10.

$L_m' \times F_{r2} \cdot \cos \alpha \sin \Delta\theta < L_f \times F_f \cdot \cos \alpha \sin \Delta\theta + L_g \times F_g \cdot \cos \alpha \sin \Delta\theta$ $L_m \times F_{r2} \cdot \cos \alpha \sin \Delta\theta < L_f \times F_f \cdot \cos \alpha \sin \Delta\theta + L_g \times F_g \cdot \cos \alpha \sin \Delta\theta$ $L_m \times F_{r2} < L_f \times F_f + L_g \times F_g$ $$L_m \times (F_f - F_g + F_m) < L_f \times F_f + L_g \times F_g \quad (9)$$

Here, since the angle $\Delta\theta$ is fine, it is considered $L_m'=L_m$ without problem.

Therefore, the range of the magnetic attracting force $F_m$ is given by the following formula (10).

$$F_m < (L_f \times F_f + L_g \times F_g)/L_m + F_g - F_f \quad (10)$$

Accordingly, $\{(L_f \times F_f + L_g \times F_g)/L_m + F_g - F_f\}$ may be taken for the upper limit value $F_{max}$ of the magnetic attracting force $F_m$ to control the magnetic attracting force $F_m$ within the range of less than this upper limit value $F_{max}$.

Note that, in the present Modification 2-3, in the distance between the axis R and an arbitrary point on the outside surface of the capsule endoscope 10, when the direction of the geometric center C is set as positive relative to the center of gravity G of the capsule endoscope 10, a value obtained by substituting a maximum value for distance $L_m$ in formula (10) may be used as the upper limit value $F_{max}$ to control the magnetic attracting force $F_m$.

Modification 2-4

Figure 29:
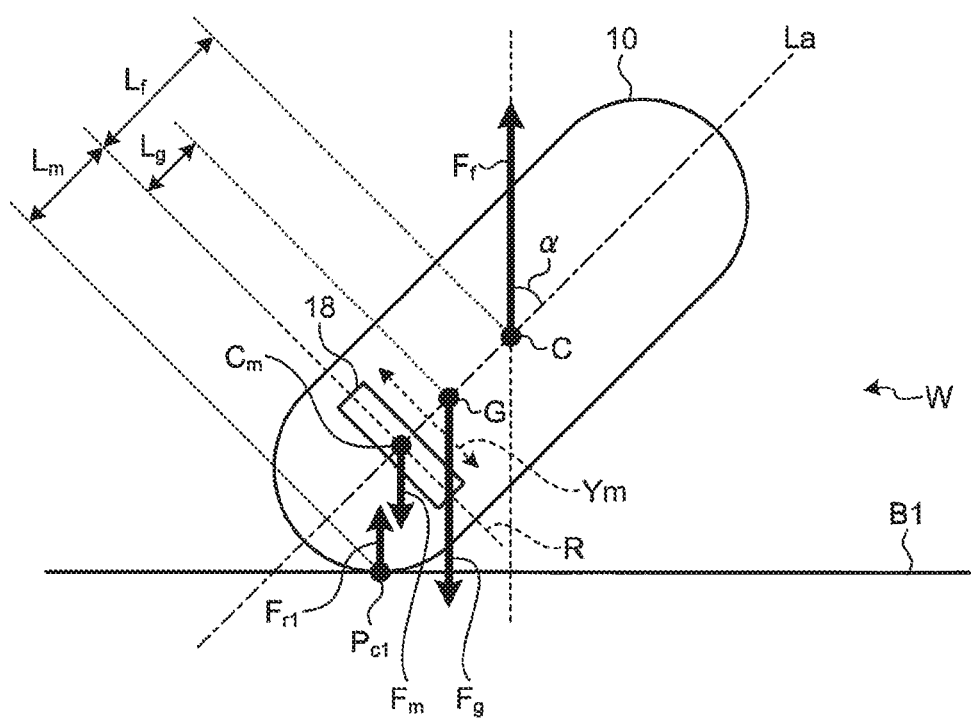
FIG. 29 is a diagram for illustrating a method of calculating an upper limit value of a magnetic attracting force according to Modification 2-4 of the second embodiment.

Next, modification 2-4 of the second embodiment of the disclosure will be described. For disposition of units constituting the capsule endoscope 10, the center of gravity G may be disposed between the geometric center C of the capsule endoscope 10 and the center $C_m$ of the permanent magnet 18, as illustrated in FIG. 29. When the capsule endoscope 10 has a specific weight smaller than that of the fluid W, for control of the posture of the capsule endoscope 10 in contact with the lower boundary surface B1, the upper limit value $F_{max}$ of the magnetic attracting force $F_m$ in the downward direction can be calculated as described below.

In this configuration, the geometric center C and the center of gravity G are positioned above the axis R, and the contact point $P_{c1}$ is positioned below the axis R. Furthermore, the relationship between the distance $L_g$ from the axis R to the center of gravity G and the distance $L_f$ from the axis R to the geometric center C is expressed as $L_f > L_g$. Furthermore, the reactive force $F_{r1}$ from the boundary surface B1 to the capsule endoscope 10 at the contact point $P_{c1}$ is expressed as $F_{r1} = F_m + F_g - F_f$.

At this time, as in the second embodiment, in order to prevent the rotation of the capsule endoscope 10, under the condition that the external force is removed, after the capsule endoscope 10 is inclined by a fine angle $\Delta\theta$ due to the external force about the axis R, relationships (11) preferably hold for the moment of force about the axis R. In the following formula, the distance $L_m'$ represents a distance between the axis R and a contact point $P_{c1}$ between the capsule endoscope 10 and the boundary surface B1, upon inclination of the capsule endoscope 10

$$L_g \times F_g \cdot \cos\alpha\sin\Delta\theta + L_m' \times F_{r1} \cdot \cos\alpha\sin\Delta\theta < L_f \times F_f \cos\alpha\sin\Delta\theta$$

$$L_g \times F_g \cdot \cos\alpha\sin\Delta\theta + L_m \times F_{r1} \cdot \cos\alpha\sin\Delta\theta < L_f \times F_f \cos\alpha\sin\Delta\theta$$

$$L_g \times F_g + L_m \times F_{r1} < L_f \times F_f$$

$$L_g \times F_g + L_m \times (F_m + F_g - F_f) < L_f - F_f \quad (11)$$

Here, since the angle $\Delta\theta$ is fine, it is considered $L_m' = L_m$ without problem.

Therefore, the range of the magnetic attracting force $F_m$ is given by the following formula (12).

$$F_m < (L_f \times F_f - L_g \times F_g)/L_m + F_f - F_g \quad (12)$$

Accordingly, $\{(L_f \times F_f - L_g \times F_g)/L_m + F_f - F_g\}$ may be taken as the upper limit value $F_{max}$ of the magnetic attracting force $F_m$ to control the magnetic attracting force $F_m$ within the range of less than this upper limit value $F_{max}$.

Note that, in the present Modification 2-4, in the distance between the axis R and an arbitrary point on the outside surface of the capsule endoscope 10, when the direction of the center of gravity G is set as positive relative to the geometric center C of the capsule endoscope 10, a value obtained by substituting a maximum value for distance $L_m$ in formula (12) may be used as the upper limit value $F_{max}$ to control the magnetic attracting force $F_m$.

Modification 2-5

Figure 30:
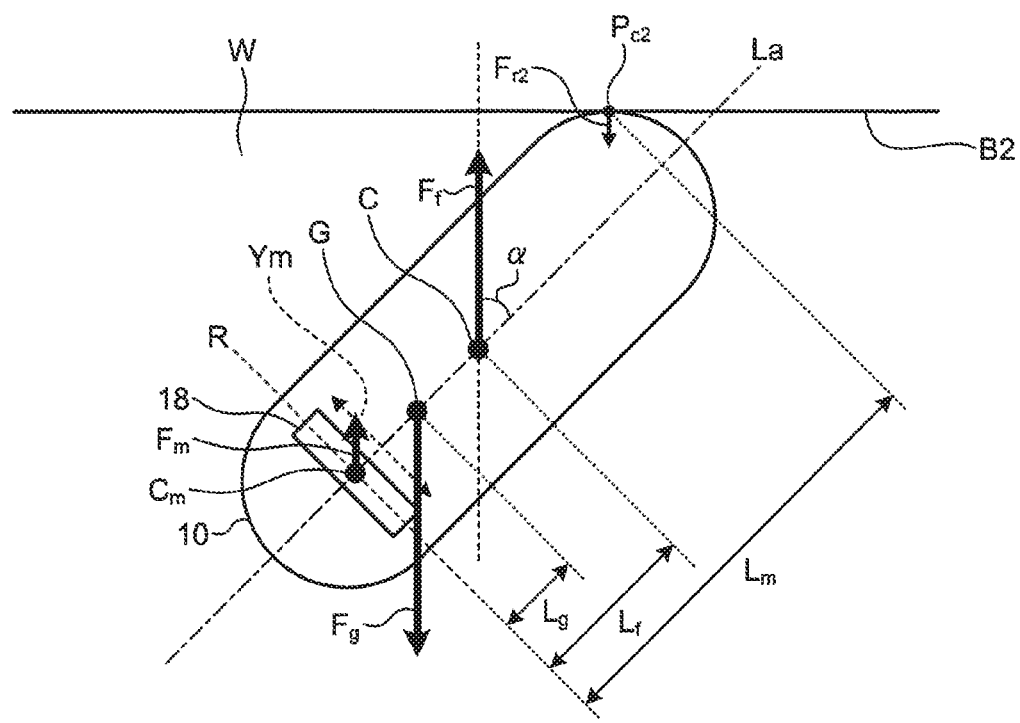
FIG. 30 is a diagram for illustrating a method of calculating an upper limit value of a magnetic attracting force according to Modification 2-5 of the second embodiment.

Next, modification 2-5 of the second embodiment of the disclosure will be described. As illustrated in FIG. 30, in the capsule endoscope 10, when the center of gravity G is disposed between the geometric center C and the center $C_m$ of the permanent magnet 18, and the capsule endoscope 10 has a specific weight larger than that of the fluid W, for control of the posture of the capsule endoscope 10 while bringing the capsule endoscope 10 into contact with the upper boundary surface B2, the upper limit value $F_m$ of the magnetic attracting force $F_m$ in an upward direction is calculated as follows.

In this configuration, the geometric center C, the center of gravity G, and the contact point $P_{c2}$ are positioned above the axis R. Furthermore, the relationship between the distance $L_g$ from the axis R to the center of gravity G and the distance $L_f$ from the axis R to the geometric center C is expressed as $L_f > L_g$. Furthermore, the reactive force $F_{r2}$ from the boundary surface B2 to the capsule endoscope 10 at the contact point $P_{c2}$ is expressed as $F_{r2} = F_f - F_g + F_m$.

At this time, as in the second embodiment, in order to prevent the rotation of the capsule endoscope 10, under the condition that the external force is removed, after the capsule endoscope 10 is inclined by a fine angle $\Delta\theta$ due to the external force about the axis R, relationships (13) preferably hold for the moment of force about the axis R. In the following formula, the distance $L_m'$ represents a distance between the axis R and a contact point $P_{c2}$ between the capsule endoscope 10 and the boundary surface B2, upon inclination of the capsule endoscope 10.

$$L_m' \times F_{r2} \cdot \cos\alpha\sin\Delta\theta + L_g \times F_g \cdot \cos\alpha\sin\Delta\theta < L_f \times F_f \cos\alpha\sin\Delta\theta$$

$$L_m \times F_{r2} \cdot \cos\alpha\sin\Delta\theta + L_g \times F_g \cdot \cos\alpha\sin\Delta\theta < L_f \times F_f \cos\alpha\sin\Delta\theta$$

$$L_m \times F_{r2} + L_g \times F_g < L_f \times F_f$$

$$L_m \times (F_f - F_g + F_m) + L_g - F_g < L_f - F_f \quad (13)$$

Here, since the angle $\Delta\theta$ is fine, it is considered $L_m' = L_m$ without problem.

Therefore, the range of the magnetic attracting force $F_m$ is given by the following formula (14).

$$F_m < (L_f \times F_f - L_g \times F_g)/L_m + F_g - F_f \quad (14)$$

Accordingly, $\{(L_f \times F_f - L_g \times F_g)/L_m + F_g - F_f\}$ may be taken as the upper limit value $F_{max}$ of the magnetic attracting force $F_m$ to control the magnetic attracting force $F_m$ within the range of less than this upper limit value $F_{max}$.

Note that, in the present Modification 2-5, in the distance between the axis R and an arbitrary point on the outside surface of the capsule endoscope 10, when the direction of the geometric center C is set as positive relative to the center of gravity G of the capsule endoscope 10, a value obtained by substituting a maximum value for distance $L_m$ in formula (14) may be used as the upper limit value $F_{max}$ to control the magnetic attracting force $F_m$.

In Modifications 2-2 to 2-5 described above, the center $C_m$ of the permanent magnet 18 may be the center of gravity G. In this configuration, in formulae (8), (10), (12), and (14), preferably $L_g = 0$.

Modification 2-6

Next, Modification 2-6 of the second embodiment will be described. In the guidance device 60 illustrated in FIG. 22, according to a type of the capsule endoscope 10 (internal disposition of component units, see FIGS. 26 to 30), the upper limit value $F_{max}$ of the magnetic attracting force $F_m$ may be used in a switchable manner.

In this configuration, formulae giving the upper limit value $F_{max}$ of the magnetic attracting force $F_m$, and parameters used in the formula are previously stored in the storage unit 27, in association with the types of the capsule endoscope 10. When a type of the capsule endoscope 10 to be used is input to the guidance device 60, at the start of examination using the capsule endoscope 10, the control unit 26A reads formulae and parameters according to the input type, from the storage unit 27, and performs control using the read formula and parameters.

Modification 2-7

Next, Modification 2-7 of the second embodiment will be described. The operation input unit 24 according to Modification 2-7 has an appearance configuration the same as the configuration illustrated in FIG. 18. When the operation information corresponding to the tilting operation of the joystick 32 indicated by the arrow Y23$j$ in (a) of FIG. 18 is input from the operation input unit 24 to the control unit 26A, the control unit 26A calculates the guidance direction and the guidance amount of the distal end of the capsule endoscope 10 on the absolute coordinate system corresponding to the tilting direction of the joystick 32, on the basis of the operation information, and controls the magnetic field generating unit 25A to generate a magnetic field having a magnetic gradient changed according to the calculated guidance direction and the guidance amount.

When the operation information corresponding to the tilting operation of the joystick 32 indicated by the arrow Y24$j$ in (a) of FIG. 18 is input from the operation input unit 24 to the control unit 26A, the control unit 26A calculates the guidance direction and the guidance amount of the distal end of the capsule endoscope 10 on the absolute coordinate system corresponding to the tilting direction of the joystick 32, on the basis of the operation information, and controls the magnetic field generating unit 25A to generate a magnetic field having a magnetic gradient changed according to the calculated guidance direction and the guidance amount.

When the operation information corresponding to the pressing operation of the up button 34U or the down button 34B indicated by the arrow Y25$j$ or Y26$j$ in (b) of FIG. 18 is input from the operation input unit 24 to the control unit 26A, the control unit 26A calculates the guidance direction and the guidance amount of the distal end of the capsule endoscope 10 on the absolute coordinate system, corresponding to pressing of any of the buttons, on the basis of the operation information, and controls the magnetic field generating unit 25A to generate a magnetic field having a magnetic gradient changed according to the guidance direction and the calculated amount.

Modification 2-8

Next, Modification 2-8 of the second embodiment will be described. For a method of detecting the position of the capsule endoscope 10 in the subject, a method of detecting an alternating magnetic field may be employed. In this configuration, as in Modification 1-4, the alternating magnetic field generation unit for generating an alternating magnetic field is provided in the capsule endoscope 10. In addition, the guidance device 60 is provided with a plurality of magnetic field sensors for detecting the alternating magnetic field.

The guidance device 60 detects the alternating magnetic field generated by the capsule endoscope 10 using a plurality of magnetic field sensors positioned at a plurality of locations to continuously calculate at least one of the position and the direction of the capsule endoscope 10 on the basis of these results of the detection.

Modification 2-9

Next, Modification 2-9 of the second embodiment will be described. For a method of detecting the position of the capsule endoscope 10 in the subject, another method of detecting the alternating magnetic field will be described. In this configuration, as in Modification 1-5, the LC circuit resonated by the alternating magnetic field is provided in the capsule endoscope 10. In addition, the guidance device 60 is provided with a plurality of magnetic field sensors for detecting the alternating magnetic field.

When the capsule endoscope 10 is not positioned in a measurement area of the subject (area of the magnetic field formed by the magnetic field generating unit 25A), the guidance device 60 previously detects the first resonance magnetic field generated by the LC circuit in the capsule endoscope 10. Then, when the capsule endoscope 10 is positioned in the measurement area in the subject, a second resonance magnetic field generated by the LC circuit in the capsule endoscope 10 is detected to continuously determine difference values between the detected value of the first resonance magnetic field and the detected value of the second resonance magnetic field. Furthermore, on the basis of these difference values, positional coordinates of the capsule endoscope 10 in a three-dimensional space are continuously calculated.

Third Embodiment

Next, a third embodiment of the disclosure will be described.

Figure 31:
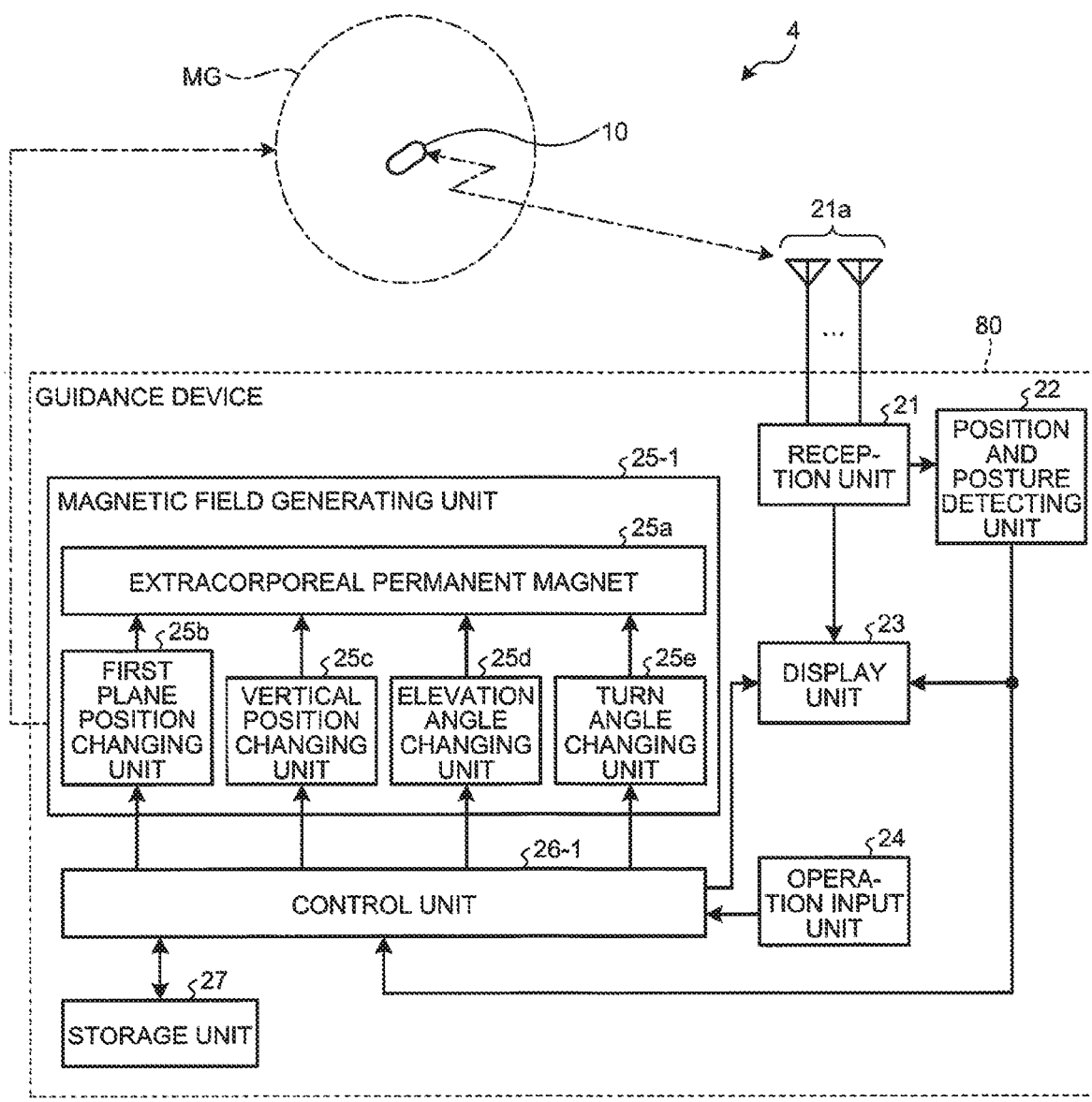
FIG. 31 is a diagram illustrating an exemplary configuration of a capsule medical device guidance system according to a third embodiment of the disclosure.

FIG. 31 is a schematic view illustrating an exemplary configuration of a capsule medical device guidance system according to the third embodiment of the disclosure. As illustrated in FIG. 31, the capsule medical device guidance system 4 according to the third embodiment includes the capsule endoscope 10 and a guidance device 80. The configuration and operation of the capsule endoscope 10 are similar to those of the first embodiment.

Instead of the magnetic field generating unit 25A illustrated in FIG. 22, the guidance device 80 includes a magnetic field generating unit 25-1 having the extracorporeal permanent magnet 25$a$ being the second magnet generating a magnetic field, the first plane position changing unit 25$b$ changing the position and the posture of the extracorporeal permanent magnet 25$a$, the vertical position changing unit 25$c$, the elevation angle changing unit 25$d$, and the turn angle changing unit 25$e$. Note that, configurations of units of the guidance device 80 other than the magnetic field generating unit 25-1 are similar to those of the second embodiment (see FIG. 22).

In the third embodiment, a control unit 26-1 controls operation of the magnetic field generating unit 25-1, on the basis of a detection result from the position and posture detecting unit 22, and the guidance instruction information received by the operation input unit 24, to change a relative position between the extracorporeal permanent magnet 25$a$ and the subject, a distance between the extracorporeal permanent magnet 25$a$ and the capsule endoscope 10, or rotation angles (elevation angle and turn angle) of the extracorporeal permanent magnet 25$a$ relative to the reference disposition, and guides the capsule endoscope 10 to a user's desired position and posture. Furthermore, at this time, the control unit 26-1 controls each unit of the magnetic field generating unit 25-1 not to generate user's unintended displacement of the capsule endoscope 10 which is generated by the rotation (change in elevation angle) of the extracorporeal permanent magnet 25$a$.

Specifically, the translation movement of the capsule endoscope 10 in the horizontal plane is achieved by moving the extracorporeal permanent magnet 25$a$ in the horizontal plane by the first plane position changing unit 25b of the guidance device 80, as in the first embodiment. Furthermore, the translation movement of the capsule endoscope 10 in the vertical direction is also achieved by moving the extracorporeal permanent magnet 25a in the vertical direction by the vertical position changing unit 25c of the guidance device 80, as in the first embodiment.

The operation of the vertical position changing unit 25c for the translation movement of the capsule endoscope 10 in the vertical direction, the operation of the elevation angle changing unit 25d for inclination of the capsule endoscope 10 relative to the gravity direction, the operation of the turn angle changing unit 25e for turning the capsule endoscope 10 inclined, about the gravity direction, and the operation of the control unit 26-1 for changing the posture of the capsule endoscope 10 floating in the fluid are similar to those in the first embodiment.

As described above, according to the third embodiment, correction of the change in vertical magnetic attracting force generated in the capsule endoscope 10, which is caused by the rotation of the extracorporeal permanent magnet 25a, allows control of the capsule endoscope 10 to have the user's desired posture while maintaining stability of the position of the capsule endoscope 10.

In the present third embodiment, as in Modification 1-1 described above, the guidance device 80 may previously define a relative displacement amount of the extracorporeal permanent magnet 25a to maintain the magnetic attracting force of the extracorporeal permanent magnet 25a in the vertical direction constant, upon changing the elevation angle of the extracorporeal permanent magnet 25a.

Furthermore, in the present third embodiment, as in Modification 1-2 described above, the guidance device 80 may include at least two guidance modes being guidance modes selectable by the user for guiding the capsule endoscope 10.

Furthermore, in the present third embodiment, the control unit 26-1 may calculate or store a distance $D_{min}$ between the capsule endoscope 10 and the extracorporeal permanent magnet 25a corresponding to the upper limit value $F_{max}$ of the magnetic attracting force, instead of calculation or storage of the upper limit value $F_{max}$ of the magnetic attracting force. In this configuration, the control unit 26-1 preferably controls the magnetic field generating unit 25-1, so that the capsule endoscope 10 and the extracorporeal permanent magnet 25a do not approach each other exceeding the stored distance $D_{min}$.

Furthermore, in the present third embodiment, the magnetic field generating unit 25-1 may further include the second plane position changing unit 25f, as in the first embodiment described above.

Other Embodiments

In the first to third embodiments and modifications thereof described above, a pantoscopic capsule having the imaging units 11A and 11B provided at both ends of the capsule endoscope 10 is employed, but a monocular capsule may be employed having an imaging unit provided at one end of the capsule endoscope. In this configuration, a capsule endoscope, in which the center of gravity G of the capsule endoscope is positioned closer to an end of the imaging unit side to image only underwater (in water), can be achieved. In contrast, a capsule endoscope, in which the center of gravity G of the capsule endoscope is positioned closer to an end of a side without the imaging unit to image only a space above the water surface, can be achieved.

Furthermore, in the imaging units 11A and 11B illustrated in FIG. 4, the imaging surfaces of the imaging elements 14A and 14B are mounted orthogonal to the major axis La, but the imaging surfaces of the imaging elements 14A and 14B may be mounted to have an angle relative to the orthogonal plane to the major axis La.

Furthermore, in the first to third embodiments and modifications thereof described above, the permanent magnet 18 is disposed so that the magnetization direction is orthogonal to the major axis La of the capsule endoscope 10, but the permanent magnet 18 may be disposed so that the magnetization direction coincides with the direction of the major axis La. At this time, the center of gravity G may be disposed at a position radially displaced from the geometric center C of the capsule endoscope 10. In this configuration, the posture of the capsule endoscope 10 can be uniquely controlled in the fluid W. Furthermore, also in this configuration, when the plane P including the geometric center C and the center of gravity G of the capsule endoscope 10, and the center $C_m$ of the permanent magnet 18, and the magnetization direction of the permanent magnet 18 are parallel with each other, the upper limit value $F_{max}$ of the magnetic attracting force, which may be generated in the capsule endoscope 10 when the capsule endoscope 10 makes contact with the boundary surface, or the distance $D_{min}$ between the capsule endoscope 10 and the extracorporeal permanent magnet 25a, can be calculated or stored in the control unit 26A, on the basis of the moment of force about the axis R passing through the center $C_m$ of the permanent magnet 18 provided in the capsule endoscope 10 (see FIG. 23), and parallel with the magnetization direction $Y_m$ of the permanent magnet 18, as in the second embodiment.

Furthermore, in the first to third embodiments and modifications thereof described above, the center of gravity G is set on the major axis La so that the capsule endoscope 10 floats while positioning the facing major axis La in the vertical direction, when the magnetic field is not applied. However, the position of the center of gravity G may be set displaced from the major axis La so that the capsule endoscope 10 floats while inclining the major axis La relative to the vertical direction, when the magnetic field is not applied. In this configuration, the azimuth angle and the inclination angle of the capsule endoscope 10 can be uniquely controlled relative to a magnetic field generated by the extracorporeal permanent magnet 25a, in the fluid W. Furthermore, also in this configuration, when the plane P including the geometric center C and the center of gravity G of the capsule endoscope 10, and the center $C_m$ of the permanent magnet 18, and the magnetization direction of the permanent magnet 18 are parallel with each other, the upper limit value $F_{max}$ of the magnetic attracting force, which may be generated in the capsule endoscope 10 when the capsule endoscope 10 makes contact with the boundary surface, or the distance $D_{min}$ between the capsule endoscope 10 and the extracorporeal permanent magnet 25a, can be calculated or stored in the control unit 26A, on the basis of the moment of force about the axis R passing through the center $C_m$ of the permanent magnet 18 provided in the capsule endoscope 10 (see FIG. 23), and parallel with the magnetization direction $Y_m$ of the permanent magnet 18, as in the second embodiment.

Furthermore, the center of gravity G of the capsule endoscope 10 may be set displaced from the geometric center C in a direction different from the magnetization direction of the permanent magnet 18. In this configuration, too, the azimuth angle and the inclination angle of the capsule endoscope 10 can be uniquely controlled relative to the magnetic field generated by the extracorporeal permanent magnet 25a, in the fluid W.

Furthermore, in the guidance devices according to the first to third embodiments and modifications thereof, for the magnetic field generation unit generating a magnetic field for guiding the capsule endoscope 10, an electromagnet (solenoidal coil) generating a magnetic field when carrying an electric current may be employed, instead of the extracorporeal permanent magnet 25a described above.

Furthermore, in the first to third embodiments and modifications thereof, the extracorporeal permanent magnet 25a having a cuboid shape is employed, but as long as the magnetization direction can be positioned on the horizontal plane, the shape of the magnet is not limited to the cuboid shape. For example, an extracorporeal permanent magnet having a disk shape or an elliptic disk shape may be employed.

According to some embodiments, the posture of the capsule medical device can be controlled, while maintaining the stable position of the capsule medical device.

The above first to third embodiments and modifications thereof are merely examples for carrying out the present invention, and the present invention is not limited to these embodiments and modifications. The present invention may create various inventions by appropriately combining a plurality of elements disclosed in the first to third embodiments and modifications thereof. The present invention can be modified in various manners in accordance with specifications, and it is obvious from the above description that other various embodiments can be made within the scope of the present invention.

What is claimed is:

1. A guidance device for guiding a capsule medical device having a magnet and introduced into a subject, the guidance device comprising:
    a magnetic field generator configured to generate a magnetic field for guiding the capsule medical device jn a vertical plane including a magnetization direction; and
    a controller configured to:
        receive a detected position and posture of the capsule medical device;
        rotate the magnetic field generator in the vertical plane including the magnetization direction of the magnetic field generator to change the posture of the capsule medical device when first operation information for changing the posture of the capsule medical device is input; and
        move the magnetic field generator in a vertical direction to change a distance between the magnetic field generator and the capsule medical device to correct a magnetic attracting force in a vertical direction of the capsule medical device, the magnetic attracting force being caused by the rotation of the magnetic field generator;
    wherein the controller is configured to:
        move the magnetic field generator in the vertical direction based on a rotation direction and a rotation amount of the magnetic field generator based on the first operation information, the detected posture of the capsule medical device when the first operation information is input, and an angle between the magnetization direction and the vertical direction of the magnetic field generator when the first operation information is input; and
        move the magnetic field generator in the vertical direction, based on a vertical magnetic attracting force generated in the capsule medical device when second operation information for moving the capsule medical device in a vertical direction is input, and a correction amount of the magnetic attracting force in the vertical direction of the capsule medical device, the magnetic attracting force being caused by the rotation of the magnetic field generator.

2. The guidance device according to claim 1, wherein the controller is configured to move the magnetic field generator in the vertical direction so that the distance between the magnetic field generator and the capsule medical device is increased with increasing angle between the magnetization direction and the vertical direction of the magnetic field generator when the first operation information is input.

3. The guidance device according to claim 1, wherein
    a rotation upper limit value as an upper limit value of a rotation speed of the magnetic field generator, and a movement upper limit value as an upper limit value of a movement speed of the magnetic field generator in the vertical direction are previously determined, and
    at least when the rotation speed based on the first operation information exceeds the rotation upper limit value, or when the movement speed based on the second operation information exceeds the movement upper limit value, the controller is configured to perform at least one of control of rotation of the magnetic field generator with the rotation upper limit value and control of movement of the magnetic field generator with the movement upper limit value.

4. The guidance device according to claim 1, wherein
    when at least one operation information of the first and second operation information is input, and then further at least one operation information of the first and second operation information is input, the controller is configured to:
        determine whether movement of the capsule medical device is stopped, which is generated by control of at least one of rotation control of the rotation magnetic field generator and movement control of movement of the magnetic field generator based on the preceding operation information; and
        perform at least one of the rotation control and the movement control based on the succeeding operation information, after determining that the movement is stopped.

5. The guidance device according to claim 4, wherein the controller is configured to:
    perform at least one of the rotation control and the movement control based on the preceding operation information; and
    determine that the movement of the capsule medical device is stopped, after a predetermined time period has elapsed since stop of the control of at least one of the rotation control and the movement control.

6. The guidance device according to claim 4,
wherein the controller is configured to determine whether the movement of the capsule medical device is stopped, based on the information about the position and the posture.

7. A capsule medical device guidance system comprising:
    the capsule medical device in which the magnet is disposed; and
    the guidance device according to claim 1.

8. The capsule medical device guidance system according to claim 7, wherein the capsule medical device has a center of gravity disposed at a position displaced from a geometric center of the capsule medical device, in a direction different from a magnetization direction of the magnet.

\* \* \* \* \*